(12) United States Patent
Piper et al.

(10) Patent No.: US 12,017,039 B2
(45) Date of Patent: Jun. 25, 2024

(54) PUMP FOR WEARABLE FLUID DELIVERY SYSTEM

(71) Applicant: Luminoah, Inc., Charlottesville, VA (US)

(72) Inventors: Joseph Neal Piper, Charlottesville, VA (US); James Landon Gilkey, Charlottesville, VA (US); Brian Bergeron, Charlottesville, VA (US); Hill Johnson, Charlottesville, VA (US); Martin Eric Weiner, Charlottesville, VA (US)

(73) Assignee: Luminoah, Inc., Charlottesville, VA (US)

( * ) Notice: Subject to any disclaimer, the term of this patent is extended or adjusted under 35 U.S.C. 154(b) by 0 days.

(21) Appl. No.: 18/446,039

(22) Filed: Aug. 8, 2023

(65) Prior Publication Data

US 2024/0050645 A1    Feb. 15, 2024

Related U.S. Application Data

(60) Provisional application No. 63/397,599, filed on Aug. 12, 2022.

(51) Int. Cl.
*A61M 5/142* (2006.01)
*F04C 2/08* (2006.01)

(52) U.S. Cl.
CPC ......... *A61M 5/14212* (2013.01); *F04C 2/084* (2013.01); *A61M 2205/6054* (2013.01); *F04C 2240/30* (2013.01)

(58) Field of Classification Search
CPC .... F04C 2/084; A61M 5/142; A61M 5/14244; F01N 3/2066; F04B 43/1253
See application file for complete search history.

(56) References Cited

U.S. PATENT DOCUMENTS

| | | | |
|---|---|---|---|
| 4,091,689 A | 5/1978 | Huffman | |
| 4,205,948 A | * 6/1980 | Jones | ................. F04B 43/1253 417/477.6 |

(Continued)

FOREIGN PATENT DOCUMENTS

| | | |
|---|---|---|
| AU | 2007/335901 | 6/2008 |
| CA | 2553335 | 8/2005 |

(Continued)

OTHER PUBLICATIONS

Sjoblom, Cindy, "Ambulatory Tube-Feeding", 2015, Umea Institute of Design, all pages.

(Continued)

*Primary Examiner* — J. Todd Newton
(74) *Attorney, Agent, or Firm* — Casimir Jones, S.C.; Brian F. Bradley

(57) ABSTRACT

A wearable fluid delivery system comprising a single-use device with a tube, a pump, and a nutrition container with a fluid. The system further includes a module including a processor, a battery, and an electric motor with an output member. The processor is configured to operate the electric motor. The single-use device is releasably coupled to the module such that the output member is coupled to the pump when the single-use device is coupled to the module, and the output member drives the pump to cause the fluid to travel through the tube.

35 Claims, 18 Drawing Sheets

(56) References Cited

U.S. PATENT DOCUMENTS

| | | | |
|---|---|---|---|
| 4,529,102 A | 7/1985 | Quinn et al. | |
| 4,640,445 A | 2/1987 | Yamada | |
| 5,074,846 A | 12/1991 | Clegg et al. | |
| 6,039,714 A | 3/2000 | Cracauer et al. | |
| 6,041,709 A * | 3/2000 | Wells | B41F 31/08 417/477.3 |
| 6,554,798 B1 | 4/2003 | Mann et al. | |
| 6,685,450 B2 | 2/2004 | Bandis et al. | |
| 6,868,987 B2 | 3/2005 | Hedington et al. | |
| 7,282,044 B2 | 10/2007 | Hudson et al. | |
| 7,896,202 B2 | 3/2011 | Greenwald et al. | |
| 8,021,322 B1 | 9/2011 | Francis | |
| 8,083,503 B2 * | 12/2011 | Voltenburg, Jr. | F04B 43/1284 417/477.2 |
| 8,133,197 B2 | 3/2012 | Blomquist et al. | |
| 8,157,813 B2 | 4/2012 | Ko et al. | |
| 8,157,816 B2 | 4/2012 | Rotella et al. | |
| 8,177,742 B1 | 5/2012 | Bagwell et al. | |
| 8,579,870 B2 | 11/2013 | Willis et al. | |
| 8,628,509 B2 | 1/2014 | Kropczynski, Jr. et al. | |
| 8,641,618 B2 | 2/2014 | Jennewine et al. | |
| 8,668,675 B2 | 3/2014 | Chase et al. | |
| 8,905,731 B2 * | 12/2014 | Baron | F04B 43/1276 604/153 |
| 8,951,232 B2 | 2/2015 | Fitzgerald et al. | |
| 9,022,653 B2 | 5/2015 | Pittet et al. | |
| 9,114,209 B2 | 8/2015 | Estes et al. | |
| 9,180,244 B2 | 11/2015 | Anderson et al. | |
| 9,468,715 B2 | 10/2016 | Tsoukalis | |
| 9,581,157 B2 | 2/2017 | Hayes-Pankhurst et al. | |
| 9,603,995 B2 | 3/2017 | Rosinko et al. | |
| 9,669,404 B2 | 6/2017 | Ortiz-Hernandez | |
| 9,682,224 B2 | 6/2017 | Downing et al. | |
| 9,724,505 B2 | 8/2017 | Williams et al. | |
| 9,852,263 B2 | 12/2017 | Harr | |
| 9,872,948 B2 | 1/2018 | Siess | |
| 9,936,877 B2 | 4/2018 | Kotz et al. | |
| 10,058,652 B2 * | 8/2018 | Tsoukalis | A61M 5/162 |
| 10,064,579 B2 | 9/2018 | Condurso et al. | |
| 10,098,628 B2 | 10/2018 | Fisher | |
| 10,420,709 B2 | 9/2019 | Davis et al. | |
| 10,426,709 B2 | 10/2019 | Harr | |
| 10,455,923 B1 | 10/2019 | Domingues et al. | |
| 10,532,835 B2 | 1/2020 | Chong et al. | |
| 10,589,014 B2 | 3/2020 | Gassman | |
| 10,682,288 B1 | 6/2020 | Elia et al. | |
| 10,813,845 B1 | 10/2020 | Juras | |
| 10,973,739 B2 | 4/2021 | Elia et al. | |
| 11,020,322 B2 | 6/2021 | Elia et al. | |
| 11,033,458 B2 | 6/2021 | Shirotani et al. | |
| 2002/0071776 A1 * | 6/2002 | Bandis | F04B 43/1253 417/477.2 |
| 2004/0007590 A1 | 1/2004 | Hedington et al. | |
| 2004/0024363 A1 | 2/2004 | Elizabeth | |
| 2005/0129545 A1 * | 6/2005 | Prosek | F04B 43/1253 417/474 |
| 2005/0135942 A1 | 6/2005 | Wood et al. | |
| 2005/0177395 A1 | 8/2005 | Blomquist | |
| 2005/0224534 A1 | 10/2005 | Hudson et al. | |
| 2006/0062672 A1 | 3/2006 | McBride et al. | |
| 2007/0106218 A1 * | 5/2007 | Yodfat | A61M 5/14248 604/152 |
| 2008/0095645 A1 | 4/2008 | Tam | |
| 2008/0103591 A1 | 5/2008 | Siess | |
| 2010/0276448 A1 | 11/2010 | Moretti | |
| 2010/0282807 A1 | 11/2010 | Sisk et al. | |
| 2012/0016295 A1 | 1/2012 | Tsoukalis | |
| 2012/0040797 A1 | 2/2012 | Fox | |
| 2012/0197192 A1 | 8/2012 | Bagwell et al. | |
| 2012/0289895 A1 | 11/2012 | Tsoukalis | |
| 2012/0289916 A1 | 11/2012 | Johansson et al. | |
| 2013/0177463 A1 | 7/2013 | Cheng | |
| 2014/0058352 A1 | 2/2014 | Francis | |
| 2014/0081202 A1 * | 3/2014 | Tsoukalis | A61M 5/142 604/153 |
| 2015/0112264 A1 | 4/2015 | Kamen et al. | |
| 2016/0030227 A1 | 2/2016 | Bronnimann et al. | |
| 2016/0138579 A1 * | 5/2016 | Norman | F04B 45/08 417/374 |
| 2016/0346169 A1 | 12/2016 | Sacchetti et al. | |
| 2017/0189614 A1 | 7/2017 | Mazlish et al. | |
| 2018/0078195 A1 | 3/2018 | Sutaria et al. | |
| 2018/0147123 A1 | 5/2018 | Sacchetti et al. | |
| 2018/0161249 A1 | 6/2018 | Elia et al. | |
| 2018/0225423 A1 | 8/2018 | Bazargan | |
| 2019/0048871 A1 | 2/2019 | Hayes-Pankhurts et al. | |
| 2019/0167531 A1 | 6/2019 | Besser et al. | |
| 2019/0168501 A1 * | 6/2019 | Wan | B41F 31/08 |
| 2019/0216688 A1 | 7/2019 | Ganter et al. | |
| 2019/0282757 A1 | 9/2019 | Gylland et al. | |
| 2019/0314249 A1 | 10/2019 | Thompson et al. | |
| 2020/0060943 A1 | 2/2020 | Elia et al. | |
| 2020/0079576 A1 | 3/2020 | Thompson et al. | |
| 2020/0163843 A1 | 5/2020 | Francis | |
| 2020/0222286 A1 | 7/2020 | Elia et al. | |
| 2020/0281819 A1 | 9/2020 | Elia et al. | |
| 2021/0015517 A1 | 1/2021 | Root et al. | |
| 2021/0037829 A1 | 2/2021 | Gupta et al. | |
| 2021/0052786 A1 | 2/2021 | Roan et al. | |
| 2021/0125719 A1 | 4/2021 | Peret et al. | |
| 2022/0087904 A1 | 3/2022 | Piper et al. | |
| 2022/0401310 A1 | 12/2022 | Piper et al. | |
| 2023/0191023 A1 | 6/2023 | Piper et al. | |

FOREIGN PATENT DOCUMENTS

| | | |
|---|---|---|
| CA | 2818220 | 6/2012 |
| CN | 107050581 | 8/2017 |
| CN | 109223574 | 1/2019 |
| DE | 102020121604 | 1/2022 |
| EP | 1862672 | 5/2007 |
| EP | 2258333 | 12/2010 |
| JP | 4485556 | 6/2010 |
| WO | WO 2005/072815 | 9/2005 |
| WO | WO 2008/075211 | 6/2008 |
| WO | WO 2013/024044 | 2/2013 |
| WO | WO 2014/049478 | 4/2014 |
| WO | WO 2015/053616 | 4/2015 |
| WO | WO 2016/160676 | 10/2016 |
| WO | WO 2017/140731 | 8/2017 |
| WO | WO 2018/108337 | 6/2018 |
| WO | WO 2018/150219 | 8/2018 |
| WO | WO 2019/145004 | 1/2019 |
| WO | WO 2020/007657 | 1/2020 |
| WO | WO 2021/046504 | 3/2021 |
| WO | WO 2021/076540 | 4/2021 |

OTHER PUBLICATIONS

Daley, Tracy, ""Tube-fed patients may be suffering due to the lack of physical activity"", 2005, ZEVEX Inc., 4 pages.

Infinity Orange Operator's Manual, Small Volume Enteral Feeding Pump, Zevex Enternal Nutirtion Delivery Systems, 2008, 54 pages.

International Search Report & Written Opinion, International Patent Application No. PCT/US2022/053470, dated Mar. 22, 2023, 10 pages.

International Search Report & Written Opinion, International Patent Application No. PCT/US2023/071838, dated Jan. 22, 2024, 16 pages.

* cited by examiner

PUMP FOR WEARABLE FLUID DELIVERY SYSTEM

CROSS REFERENCE TO RELATED APPLICATIONS

This application claims priority to U.S. Provisional Patent Application No. 63/397,599, filed Aug. 12, 2022, which is incorporated herein by reference in its entirety.

BACKGROUND

Enteral nutrition, or tube feeding, is a process that delivers nutrition directly to the stomach or small intestine in place of traditional oral feeding. If a patient is receiving treatment outside of a hospital setting, the process is referred to as Home Enteral Nutrition (HEN). A 2013 study indicates that as many as 250,000 adults and 190,000 children currently require HEN as a part of their medical treatment in the United States. Currently, the leading conditions that indicate a need for HEN include cancer, nonmalignant respiratory disease, and neurological disorders. Enteral nutrition currently requires an array of medical resources and technologies including doctor assessment, a nutrition plan prescribed by a nutrition support team, a surgically implanted gastrostomy tube, a delivery system, tubing sets, and a nutritional formula. Medical patients for whom oral feeding is not allowable or sufficient commonly benefit from prescribed enteral nutrition. This form of therapy delivers nutrition directly to a patient's gastrointestinal tract (GI) through man-made tubes that are placed into the GI tract. In order to access any portion of the patient's GI tract, the placed tubes must enter the patient's body through incisions created in the patient's abdominal wall or through existing body cavities such as the nasal cavity.

The distal end of any such tube is placed in the GI tract, while the proximal end of any such tube remains outside of the patient's body, permitting the proximal end to interface with enteral nutrition delivery technology. Surgically implanted tubes are generally indicated for long-term enteral nutrition needs while nasally placed tubes are indicated for short-term (less than two months) needs or when a patient is not healthy enough to tolerate surgery. Commonly, gastrostomy tubes are placed one of three ways: (1) surgically, through an open procedure or laparoscopically, (2) endoscopically, or (3) radiologically with a percutaneous insertion procedure.

Malnutrition and dysphagia are increasing, especially in chronic disease patients and elderly people. The occurrence of malnutrition is high in patients with chronic illnesses like cancer, neurological disorders, heart failure, and COPD, and increases with age as well. The prevalence of various cancers, especially gastric, head and neck/throat, and esophageal cancers, is growing globally, correlating to a rise in the need for enteral feeding in some oncology patients. Also, there is an increase in new markets where enteral feeding is playing a role for the first time. These include areas such as sports medicine and athletic training, pregnant women who suffer from hyperemesis gravidarum, and treatment for bulimia/anorexia conditions.

SUMMARY

The disclosure provides, in one aspect, a pump comprising: a housing, a carrier positioned within the housing, and a plurality of planet gears coupled to the carrier. The pump further includes a receptacle positioned between the plurality of planet gears. The pump further includes a tube with an inlet portion, an outlet portion, and an intermediate portion positioned between the inlet portion and the outlet portion. At least one of the plurality of planet gears is in contact with the intermediate portion of the tube.

In some embodiments, the receptacle is configured to receive a drive gear mounted on a drive module.

In some embodiments, the housing includes an aperture aligned with receptacle, wherein the aperture defines a center axis.

In some embodiments, each of the plurality of planet gears define a planet axis spaced from and parallel to the center axis.

In some embodiments, the carrier at least partially defines the receptacle positioned between the plurality of planet gears.

In some embodiments, the receptacle defines a center axis and wherein the housing includes an aperture aligned with the receptacle.

In some embodiments, each of the plurality of planet gears define a planet axis spaced from and parallel to the center axis.

In some embodiments, the pump further includes a gear positioned within the carrier, wherein the gear is aligned with the center axis.

In some embodiments, the gear is enmeshed with the plurality of planet gears.

In some embodiments, a portion of each of the plurality of planet gears extends from the carrier.

In some embodiments, each of the plurality of planet gears includes gear teeth in direct contact with the tube.

In some embodiments, the housing includes a ring gear portion and the plurality of planet gears is enmeshed with the ring gear portion.

In some embodiments, the ring gear portion is a first ring gear portion and the housing further includes a second ring gear portion and a channel positioned between the first ring gear portion and the second ring gear portion, and wherein the tube is positioned at least partially within the channel.

In some embodiments, each of the plurality of planet gears is enmeshed with the first ring gear portion and the second ring gear portion.

In some embodiments, the housing includes an outer surface with a groove formed in the outer surface.

In some embodiments, the inlet portion extends at an inlet axis, and the outlet portion extends at an outlet axis, and wherein the inlet axis and the outlet axis intersect at angle.

In some embodiments, the angle is 90 degrees.

In some embodiments, the pump further includes a wireless identification tag positioned within the housing.

In some embodiments, the housing includes a cutout configured to at least partially receive a sensor.

In some embodiments, the inlet portion includes a first removable connector and the outlet portion includes a second removable connector.

The disclosure provides, in one aspect, a nutrition container comprising a first wall panel and a second wall panel coupled to the first wall panel. The first wall panel includes a channel that extends away from the second wall panel. A cavity is at least partially formed by the first wall panel, the second wall panel, and the channel.

In some embodiments, the second wall panel is coupled to the first wall panel along a perimeter.

In some embodiments, the perimeter includes a first end, a second end opposite the first end, a first side, and a second side opposite the first side.

In some embodiments, the channel is a first channel, and the first wall panel further includes a second channel that extends away from the second wall panel.

In some embodiments, the second channel is in fluid communication with the first channel.

In some embodiments, the first channel is oriented along a first axis and the second channel is oriented along a second axis, wherein the second axis intersects the first axis at a first angle.

In some embodiments, the first wall panel further includes a third channel that extends away from the second wall panel, wherein the third channel is oriented along a third axis. The third axis intersects the first axis a second angle, the second angle smaller than the first angle.

In some embodiments, the first wall panel and the second wall panel are identical.

In some embodiments, the nutrition container further includes an adapter positioned between the first wall panel and the second wall panel.

In some embodiments, the adapter includes a body and a stem extending from the body, wherein a first aperture is formed on the body and is in fluid communication with the cavity, and wherein a second aperture is formed on the stem.

In some embodiments, the nutrition container further includes a fluid positioned within the cavity.

The disclosure provides, in one aspect, a single-use device comprising a nutrition container defining a cavity and a fluid contained within the cavity. The single-use device also includes a tube with an inlet and an outlet, wherein the inlet is fluidly coupled to the cavity. The single-use device also includes a pump coupled to the nutrition container and the tube. Operation of the pump causes the fluid to travel from the inlet to the outlet.

In some embodiments, the tube is removably coupled to the nutrition container.

In some embodiments, the single-use device further includes a breakaway coupling coupled to the tube between the inlet and the outlet.

In some embodiments, the nutrition container includes a wall panel and a channel formed in the wall panel, wherein the channel at least partially defines the cavity.

In some embodiments, the nutrition container includes an adaptor with a stem at least partially received within the pump.

In some embodiments, the pump includes a housing and a plurality of planet gears positioned within the housing.

In some embodiments, the plurality of planet gears is in direct contact with the tube.

In some embodiments, the housing is integrally formed with the nutrition container.

In some embodiments, the housing includes a groove configured to receive a detent.

In some embodiments, the pump further includes a receptacle to receive a drive gear positioned on a separate module.

In some embodiments, the tube has a length extending from the pump of no more than 20 cm.

In some embodiments, the single-use device further includes a connector coupled to an end of the tube, the connector configured to couple to a patient.

In some embodiments, the single-use device further includes a machine-readable identifier representative of a characteristic of the fluid.

In some embodiments, the characteristic is a volume, a caloric count, or a nutritional value.

The disclosure provides, in one aspect, a system comprising: a single-use device including a tube, a pump, and a nutrition container with a fluid. The system further includes a module including a processor, a battery, and an electric motor with an output member. The processor is configured to operate the electric motor. The single-use device is releasably coupled to the module such that the output member is coupled to the pump when the single-use device is coupled to the module. The output member drives the pump to cause the fluid to travel through the tube.

In some embodiments, the system further includes a wearable fastener that at least partially receives the module or the single-use device.

In some embodiments, the wearable fastener is an elastic band configured to surround a waist of a user.

In some embodiments, the wearable fastener is a mount with a magnet and a clip.

In some embodiments, the output member is received within the pump.

In some embodiments, the module includes a sensor configured to detect when the single-use device is coupled to the module.

In some embodiments, the processor does not energize the electric motor unless the sensor detects the single-use device is coupled to the module.

In some embodiments, the module includes a recess and the pump is at least partially received within the recess.

In some embodiments, the pump includes a groove and the module includes a detent configured to be received within the groove when the single-use device is coupled to the module.

In some embodiments, the module includes a sensor configured to determine the acceleration or orientation of the module.

In some embodiments, the system further includes a sensor configured to detect the pressure within the tube.

In some embodiments, the sensor is at least partially positioned within the tube.

In some embodiments, the module includes an optical sensor having a recess; wherein the tube is at least partially positioned within the recess.

In some embodiments, a housing of the pump at least partially covers the optical sensor.

In some embodiments, the pump further includes a wireless identification tag positioned within the housing, and the module further includes a reader configured to detect the wireless identification tag.

Other aspects of the disclosure will become apparent by consideration of the detailed description and accompanying drawings.

Definitions

As used herein, the terms "processor" and "central processing unit" or "CPU" are used interchangeably and refer to a device that is able to read a program from a computer memory (e.g., ROM or other computer memory) and perform a set of steps according to the program. As used herein, the term "processor" (e.g., a microprocessor, a microcontroller, a processing unit, or other suitable programmable device) can include, among other things, a control unit, an arithmetic logic unit ("ALC"), and a plurality of registers, and can be implemented using a known computer architecture (e.g., a modified Harvard architecture, a von Neumann architecture, etc.). In some embodiments the processor is a microprocessor that can be configured to communicate in a stand-alone and/or a distributed environment, and can be configured to communicate via wired or wireless communications with other processors, where such one or more processor can be configured to operate on one or more processor-controlled devices that can be similar or different devices.

As used herein, the term "memory" is any memory storage and is a non-transitory computer readable medium. The memory can include, for example, a program storage area and the data storage area. The program storage area and the data storage area can include combinations of different types of memory, such as a ROM, a RAM (e.g., DRAM, SDRAM, etc.), EEPROM, flash memory, a hard disk, a SD card, or other suitable magnetic, optical, physical, or electronic memory devices. The processor can be connected to the memory and execute software instructions that are capable of being stored in a RAM of the memory (e.g., during execution), a ROM of the memory (e.g., on a generally permanent bases), or another non-transitory computer readable medium such as another memory or a disc. In some embodiments, the memory includes one or more processor-readable and accessible memory elements and/or components that can be internal to the processor-controlled device, external to the processor-controlled device, and can be accessed via a wired or wireless network. Software included in the implementation of the methods disclosed herein can be stored in the memory. The software includes, for example, firmware, one or more applications, program data, filters, rules, one or more program modules, and other executable instructions. For example, the processor can be configured to retrieve from the memory and execute, among other things, instructions related to the processes and methods described herein.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks, whether local or distant (e.g., cloud-based).

"About" and "approximately" are used to provide flexibility to a numerical range endpoint by providing that a given value may be "slightly above" or "slightly below" the endpoint without affecting the desired result.

The term "coupled," as used herein, is defined as "connected," although not necessarily directly, and not necessarily mechanically. The term coupled is to be understood to mean physically, magnetically, chemically, fluidly, electrically, or otherwise coupled, connected or linked and does not exclude the presence of intermediate elements between the coupled elements absent specific contrary language.

As used herein, the term "in electronic communication" refers to electrical devices (e.g., computers, processors, etc.) that are configured to communicate with one another through direct or indirect signaling. Likewise, a computer configured to transmit (e.g., through cables, wires, infrared signals, telephone lines, airwaves, etc.) information to another computer or device, is in electronic communication with the other computer or device. As used herein, the term "transmitting" refers to the movement of information (e.g., data) from one location to another (e.g., from one device to another) using any suitable means.

As used herein, the term "network" generally refers to any suitable electronic network including, but not limited to, a wide area network ("WAN") (e.g., a TCP/IP based network), a local area network ("LAN"), a neighborhood area network ("NAN"), a home area network ("HAN"), or personal area network ("PAN") employing any of a variety of communications protocols, such as Wi-Fi, Bluetooth, ZigBee, etc. In some embodiments, the network is a cellular network, such as, for example, a Global System for Mobile Communications ("GSM") network, a General Packet Radio Service ("GPRS") network, an Evolution-Data Optimized ("EV-DO") network, an Enhanced Data Rates for GSM Evolution ("EDGE") network, a 3GSM network, a 4GSM network, a 5G New Radio, a Digital Enhanced Cordless Telecommunications ("DECT") network, a digital AMPS ("IS-136/TDMA") network, or an Integrated Digital Enhanced Network ("iDEN") network, etc.

As used herein, the term "subject" or "patient" refers to any animal (e.g., a mammal), including, but not limited to, humans, non-human primates, companion animals, livestock, equines, rodents, and the like, which is to be the recipient of a particular treatment. Typically, the terms "subject" and "patient" are used interchangeably herein in reference to a human subject.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

In the foregoing description of preferred embodiments, specific terminology has been resorted to for the sake of clarity. However, the invention is not intended to be limited to the specific terms so selected, and it is to be understood that each specific term includes all technical equivalents which operate in a similar manner to accomplish a similar technical purpose. Terms such as "top" and "bottom", "front" and "rear", "inner" and "outer", "above", "below", "upper", "lower", "vertical", "horizontal", "upright" and the like are used as words of convenience to provide reference points.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

Before any embodiments are explained in detail, it is to be understood that the invention is not limited in its application to the details of construction and the arrangement of components set forth in the following description or illustrated in the following drawings. The invention is capable of other embodiments and of being practiced or of being carried out in various ways.

DETAILED DESCRIPTION

Despite claims of portability, conventional equipment and methods for HEN mobility are an afterthought in the form of, for example, inadequate, over-priced backpacks. Although backpacks appear to provide patients with increased mobility, treatments often fail when the pump is not positioned on an IV stand with a stationary patient. Mechanical failures of the device may also occur and may include the occlusion of tubing as a result of kinking or viscous formula and/or the malalignment of the feeding bag in the backpack causing flow to be interrupted. As a result of these mobility issues during feeds, it is estimated that the average person is required to sit at least 3 hours per day to reach their required nutrition. Accordingly, the need exists for an improved portable enteral nutrition system.

Such a wearable fluid delivery system is described in U.S. patent application Ser. No. 17/478,905, filed Sep. 18, 2021, the entire contents of which are incorporated herein by reference. Also, a wearable fluid delivery system providing regimen-predictive analytics is described in U.S. patent application Ser. No. 17/645,181, filed on Dec. 20, 2021, the entire contents of which are incorporated herein by reference.

Figure 1:
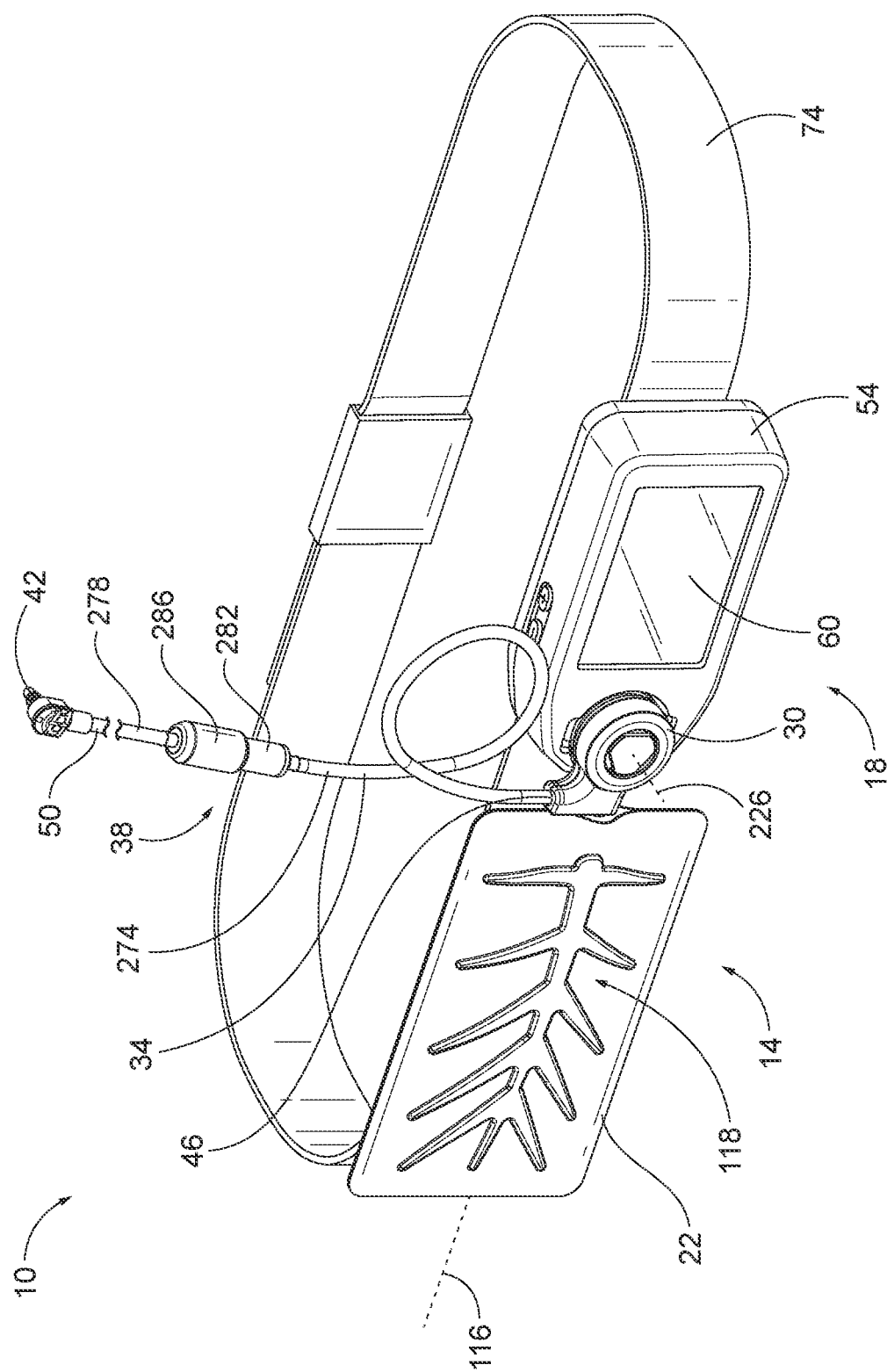
FIG. 1 is a perspective view of a wearable fluid delivery system including a pouch assembly, a module, and a wearable fastener.

With reference to FIG. 1, provided herein is wearable fluid delivery system 10. In some embodiments, the wearable fluid delivery system 10 is portable and utilized for intermittent infusions, continuous infusions, or night feeds. The system 10 allows the patient full or near-full mobility as nutritive fluids are administered. In this way, a patient may find the product useful in their everyday life, as it may grant them autonomy by untethering them from a pole and machine that requires them to be immobile. In addition, the system is a safer alternative than existing solutions because it takes away the risk of having tension applied to the extra slack of tubing, a situation which may cause problems with safety and efficacy.

The system 10 includes a pouch assembly 14, which is a single-use device (e.g., a single use disposable), and a module 18, which is reusable. The system 10 includes disposable elements (e.g., the disposable pouch assembly 14) that may be replaced after each feeding, for example.

The pouch assembly 14 includes a nutrition container 22 with a fluid (e.g., a fluid reservoir) contained within a cavity 26 defined by the container 22. In some embodiments, the fluid is a nutrient fluid, a medication, or other therapeutic fluid, that is pumped from the nutrition container 22 for delivery to the user. In some embodiments, the nutrition container 22 is pre-filed with the fluid. In other embodiments, a user is able to fill the nutrition container 22 with a fluid.

With continued reference to FIG. 1, the pouch assembly 14 also includes a pump 30, a tube 34, a breakaway coupling 38, and an end connector 42. The tube 34 includes an inlet 46 coupled to the pump 30 and an outlet 50 coupled to the end connector 42. The inlet 46 of the tube 34 is fluidly coupled to the cavity 26 through the pump 30. As detailed herein, the pump 30 is coupled to the nutrition container 22 and the tube 34, and operation of the pump 30 causes the fluid in the cavity 26 to travel from the inlet 46 to the outlet 50. The pump 30 produces necessary flow rates for delivering nutrition regardless of the orientation of the user and/or orientation of the pouch assembly 14.

Figure 9:
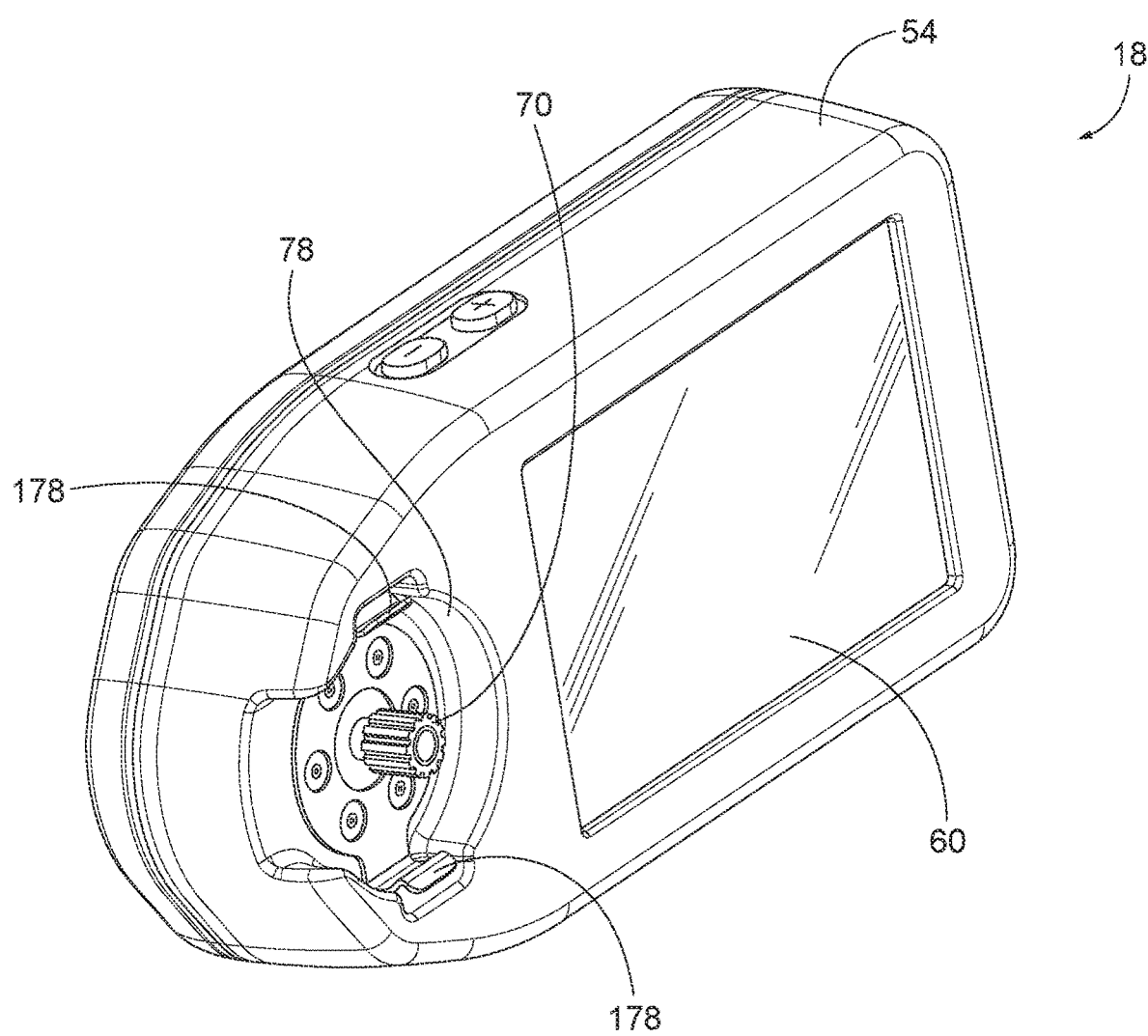
FIG. 9 is a perspective view of the module of FIG. 1.
Figure 10:
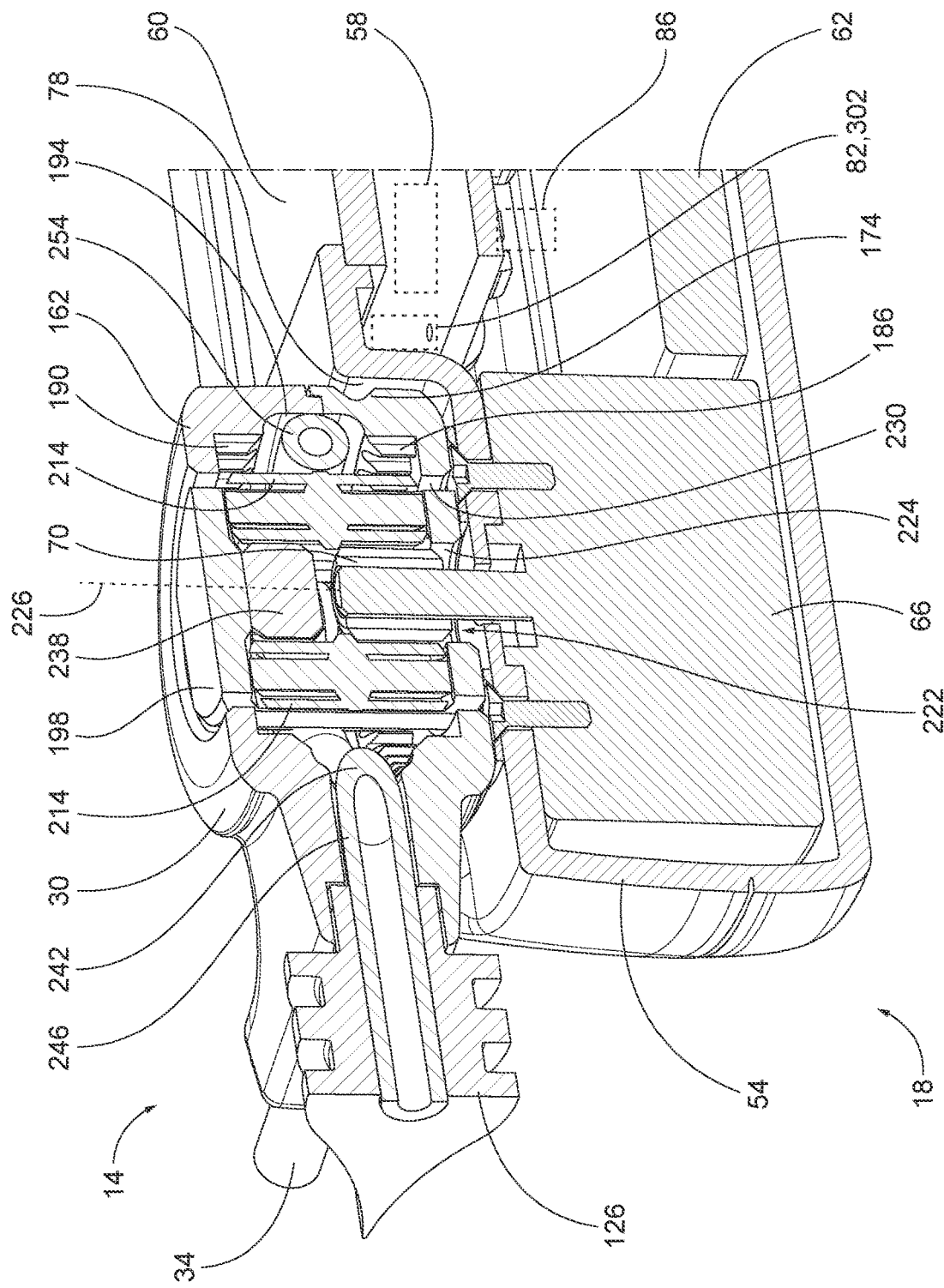
FIG. 10 is a partial cross-sectional view of the pouch assembly mounted on the module of FIG. 1.

With reference to FIGS. 9 and 10, the module 18 includes a housing 54, a processor 58, a display 60, a battery 62, and an electric motor 66. In the illustrated embodiment, the electric motor 66 includes an output member 70 driven in response to activation of the electric motor 66. The processor 58 is configured to operate the electric motor 66 and drive the output member 70. In the illustrated embodiment, the output member 70 is a pinion gear. In some embodiments, the output member 70 is a self-aligning pinion gear. In some embodiments, the output member 70 is made of a wear-resistant material (e.g., a copy alloy, an iron alloy, an aluminum alloy, a thermoplastic, etc.). As detailed herein, the output member 70 (and the module 18) is reusable and as such may be suitable as a higher-cost component.

With reference to FIG. 1, the system 10 includes a wearable fastener 74 that at least partially receives the module 18 and/or the pouch assembly 14. In some embodiments, the wearable fastener 74 is an elastic band configured to surround a waist of a user. In other embodiments, the wearable fastener is a vest, a sash, an over-shoulder design, or integrated into conventional clothing (e.g., T-shirt, sweatshirt, etc.).

Figure 2:
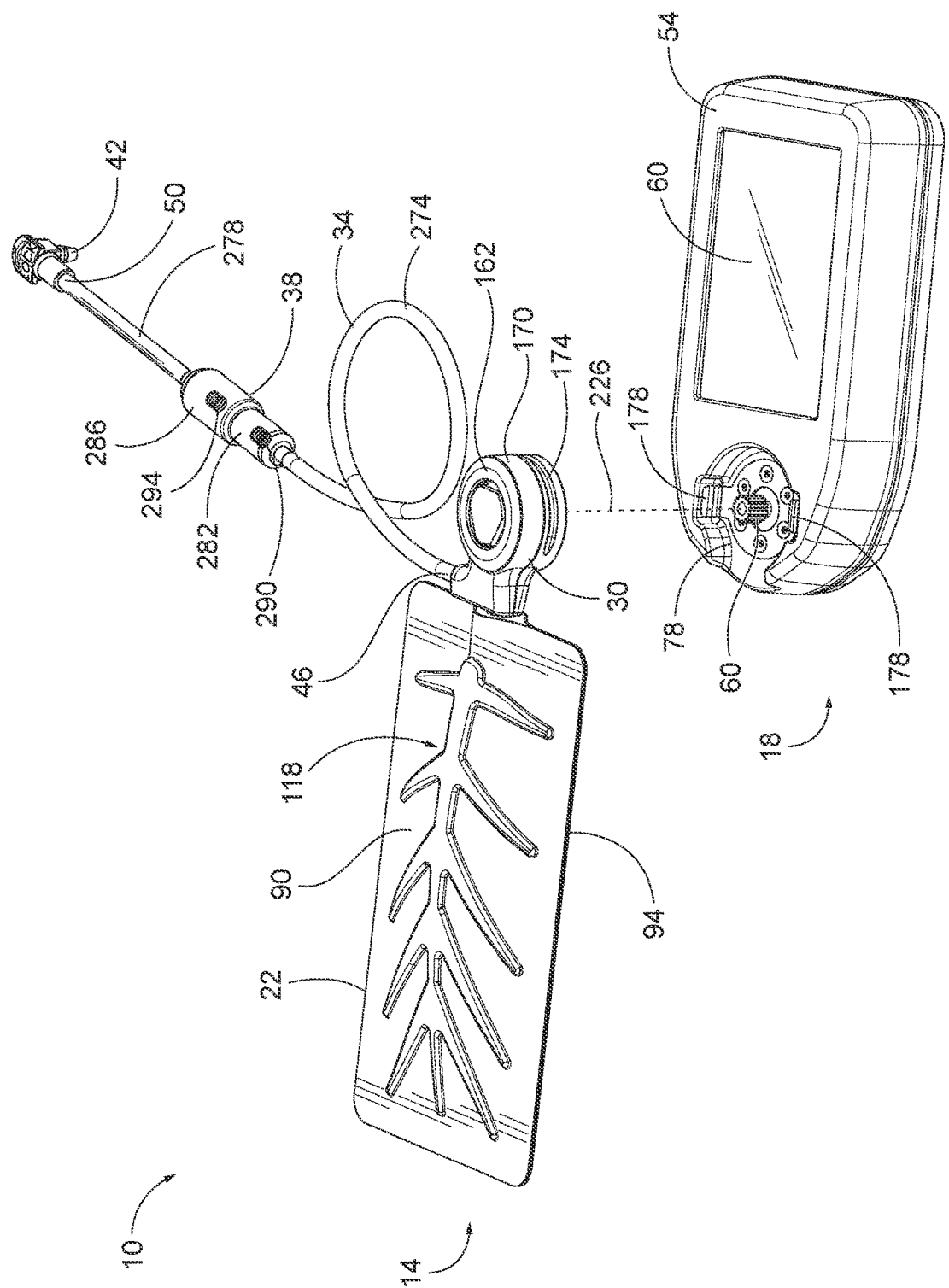
FIG. 2 is a perspective view of the pouch assembly removed from the module of FIG. 1.

With reference to FIG. 2, the pouch assembly 14 is releasably coupled to the module 18. In the illustrated embodiment, the module 18 includes a recess 78 formed in the housing 54, and the pump 30 is at least partially received within the recess 78. In some embodiments, the recess 78 is shaped such that it is not possible for a user to mount the pouch assembly 14 on the module 18 in an incorrect orientation. The output member 70 (e.g., the pinon gear driven by the electric motor 66) is coupled to the pump 30 when the pouch assembly 14 is coupled to the module 18. In the illustrated embodiment, the output member 70 is at least partially received within the pump 30 when the pouch assembly 14 is mounted to the module 18. As detailed herein, the output member 70 drives the pump 30 to cause the fluid from the cavity 26 to travel through the tube 34.

In some embodiments, the module 18 includes a sensor 82 configured to detect when the pouch assembly 14 is coupled to the module 18. In some embodiments, the sensor 82 is a capacitive sensor or an optical sensor. In some embodiments, the processor 58 does not energize the electric motor 66 unless the sensor 82 detects the pouch assembly 14 is coupled to the module 18. In other words, the sensor 82 and the processor 58 lockout the energization of the electric motor 66 when the pouch assembly 14 is not coupled, or not coupled properly, to the module 18. In some embodiments, the module 18 includes a sensor 86 configured to determine the acceleration and/or the orientation of the module 18. In some embodiments, the sensor 86 is an accelerometer or gyroscope. Information gathered by various sensors of the module 18 are utilized, in some embodiments, by the processor to more efficiently or effectively operate the pump 30 via the electric motor 66.

Figure 5:
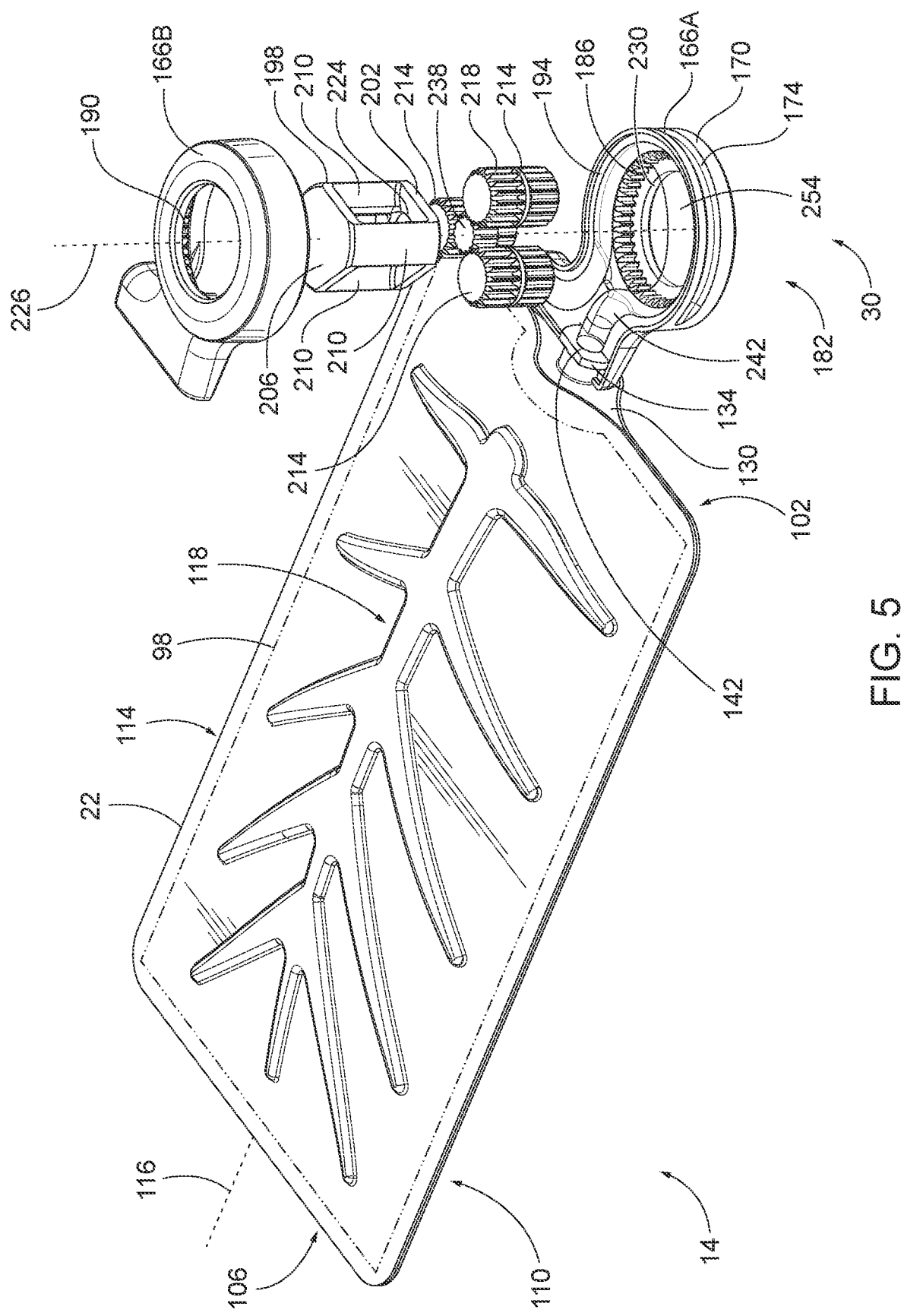
FIG. 5 is an exploded view of the pouch assembly of FIG. 1.

With reference to FIGS. 3-6, the pouch assembly 14 includes the nutrition container 22 (e.g., reservoir, pouch, bag, vessel, etc.). The nutrition container 22 includes a first wall panel 90 and a second wall panel 94 coupled to the first wall panel 90. In the illustrated embodiment, the second wall panel 94 is coupled to the first wall panel 90 along a perimeter 98 (FIG. 5). In some embodiments, the second wall panel 94 and the first wall panel 90 are welded together along the perimeter 98. The perimeter 98 includes a first end 102, a second end 106 opposite the first end 102, a first side 110, and a second side 114 opposite the first side 110. In the illustrated embodiment, the first end 102 is positioned closer to the pump 30 than the second end 106. In the illustrated embodiment, the nutrition container 22 is rectangular shaped. In some embodiments, the first and second sides 110, 114 are each longer than the first and second end 102, 106. In the illustrated embodiment, the nutrition container 22 extends along a longitudinal axis 116 (FIG. 5). In some embodiments, the wall panels 90, 94 of the nutrition container 22 are made of polyvinyl chloride (PVC), Mylar (e.g., biaxially-oriented polyethylene terephthalate), other suitable composites, or a blend such.

The first wall panel 90 includes a first plurality of channels 118 (e.g., 118A-118K) and the second wall panel 94 includes a second plurality of channels 122. As such, the cavity 26 is at least partially formed by the first wall panel 90, the second wall panel 94, and the channels 118, 122. In other words, the cavity 26 is an internal volume defined by the wall panels 90, 94 and the channels 118, 122 formed in the wall panels 90, 94. As detailed herein, the fluid is positioned within the cavity 26, and the nutrition container 22 provides for gravity-independent complete expulsion of the fluid. In other words, the nutrition container 22 is configured to operate in any orientation and ensures complete extraction of the fluid from the cavity 26. Conventional nutrition containers collapse onto themselves under pressure, trap fluid within the container, and result in incomplete extraction of fluid. As such, all fluid within the cavity 26 of the nutrition container is fully expelled, even if the fluid is flowing against the force of gravity.

In some embodiments, the plurality of channels is formed as additional tubing implemented into the surface of the nutrition container. In some embodiments, the plurality of channels is configured in a branched arrangement that bolsters the structural integrity of the pouch.

In some embodiments, the pouch assembly 14 includes an adapter 126 positioned between the first wall panel 90 and the second wall panel 94. In the illustrated embodiment, the adapter 126 is positioned at the first end 102 and secured between the wall panels 90, 94. In some embodiments, the adapter 126 is welded between the wall panels 90, 94. The adapter 126 includes a body 130 and a stem 134 extending from the body 130. As detailed herein, the stem 134 is at least partially received within the pump 30. A first aperture 138 is formed on the body 130 and is in fluid communication with the cavity 26. A second aperture 142 is formed on the stem 134. A fluid passageway 146 (FIG. 4) extends between the first aperture 138 and the second aperture 142. In some embodiments, an intake tube is coupled to the first aperture 138 and extends into the cavity 26 (e.g., is positioned within the cavity 26).

Figure 3:
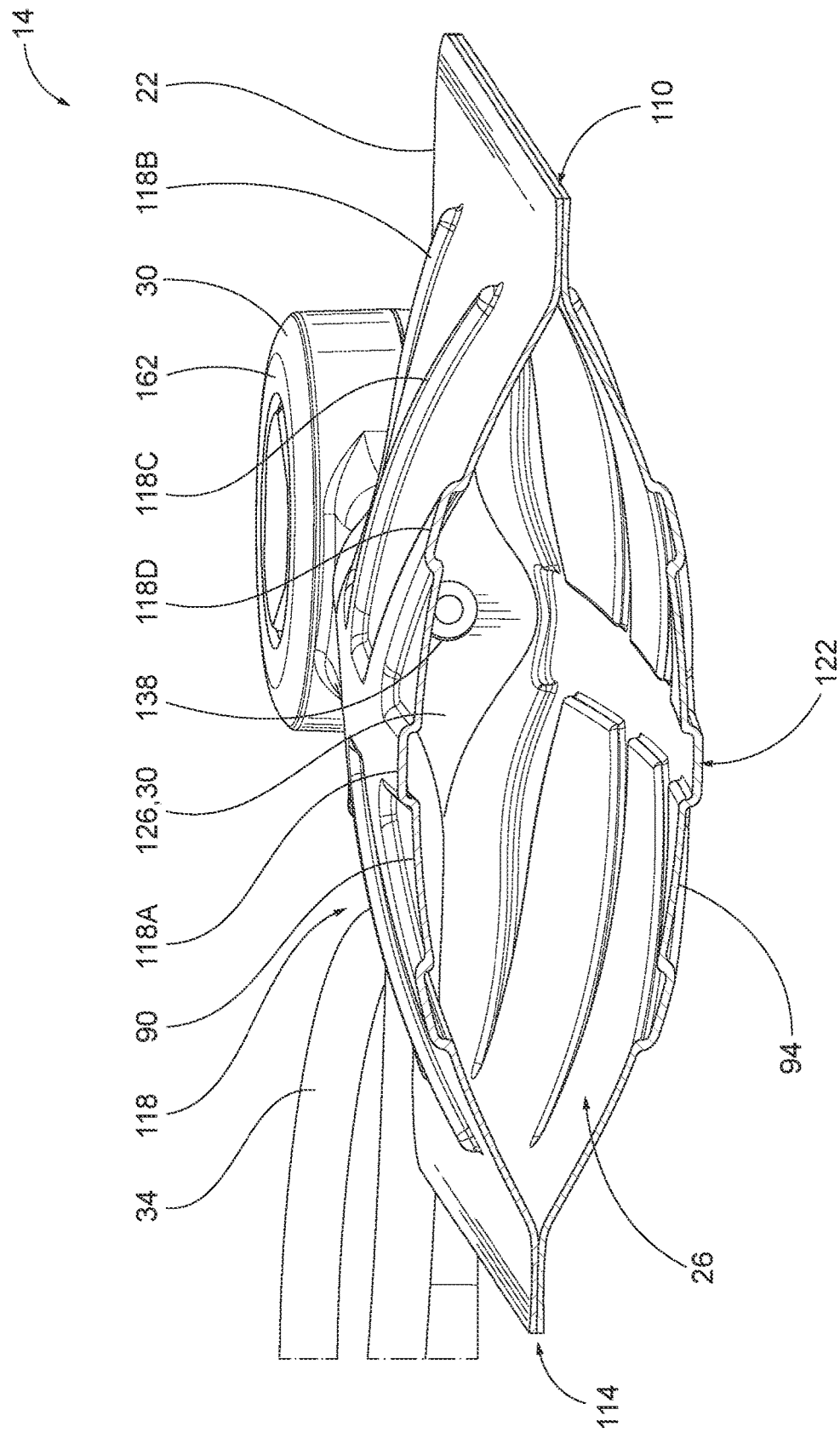
FIG. 3 is a perspective view of a cross-section through the pouch assembly of FIG. 1.
Figure 4:
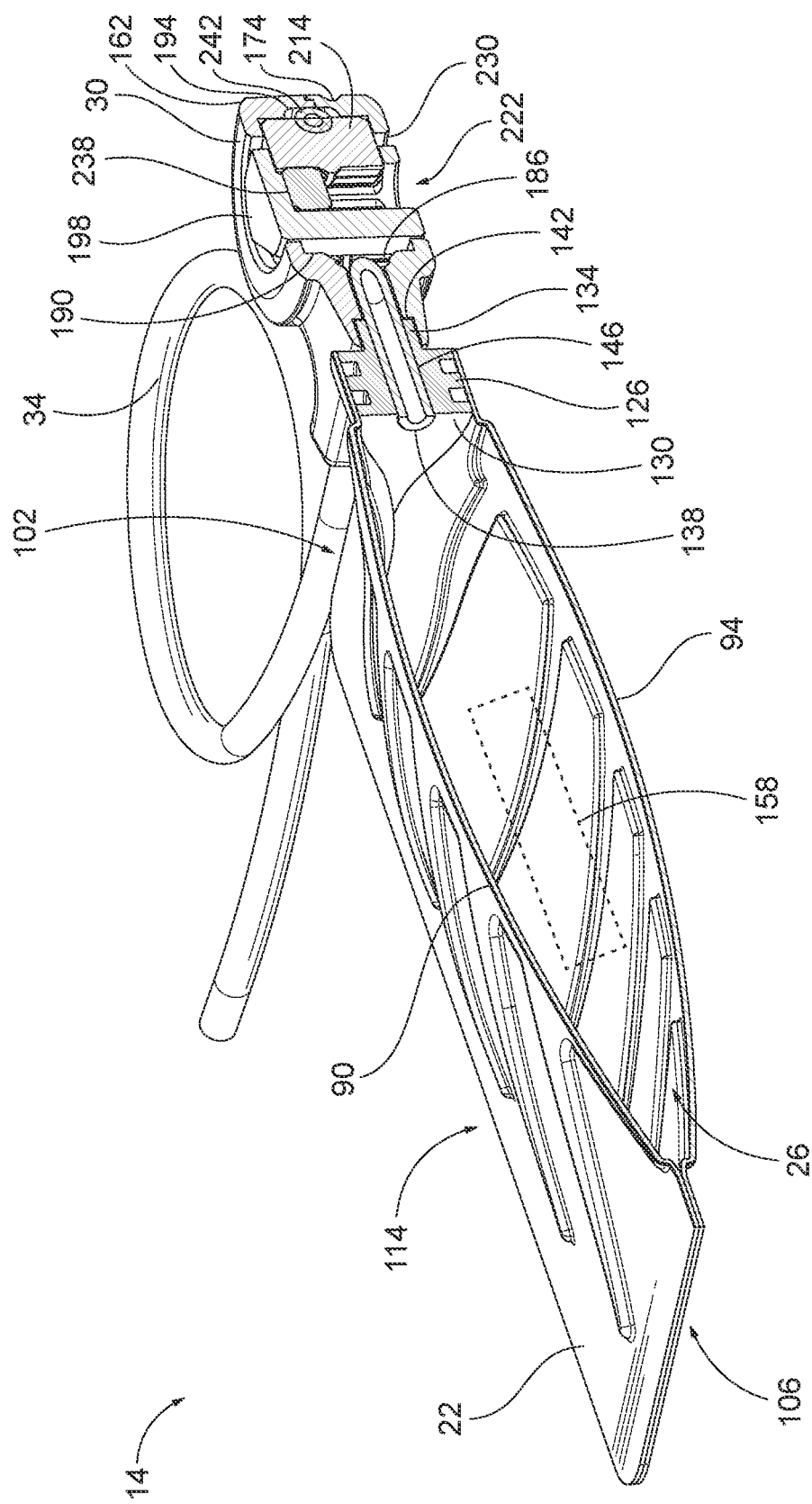
FIG. 4 is a perspective view of a cross-section through the pouch assembly of FIG. 1.

With reference to FIG. 3, the first plurality of channels 118 (e.g., 118A-118K) in the first wall panel 90 extend away from the second wall panel 94. In other words, the channels 118 are embossed in the first wall panel 90 such that the channels 118 are recessed in a direction away from the second wall panel 94—expanding the volume of the cavity 26. For example, the first wall panel 90 includes a first channel 118A that extends away from the second wall panel 94 and a second channel 118B that extends away from the second wall panel 94. In the illustrated embodiment, the second channel 118B is in fluid communication with the first channel 118A. The channels 118 further include a third channel 118C, a fourth channel 118D, a fifth channel 118E, and a sixth channel 118F in fluid communication with the first channel 118A. In the illustrated embodiment, the channels 118B-118F are spaced apart from each other along the first channel 118A. Channels 118G-118K are positioned on an opposite side of the channel 118A as channels 118B-118F, are in fluid communication with the first channel 118A. In the illustrated embodiment, channels 118G-118K are a mirror image of channels 118B-118F, with the first channel 118A being the line of symmetry.

Figure 6:
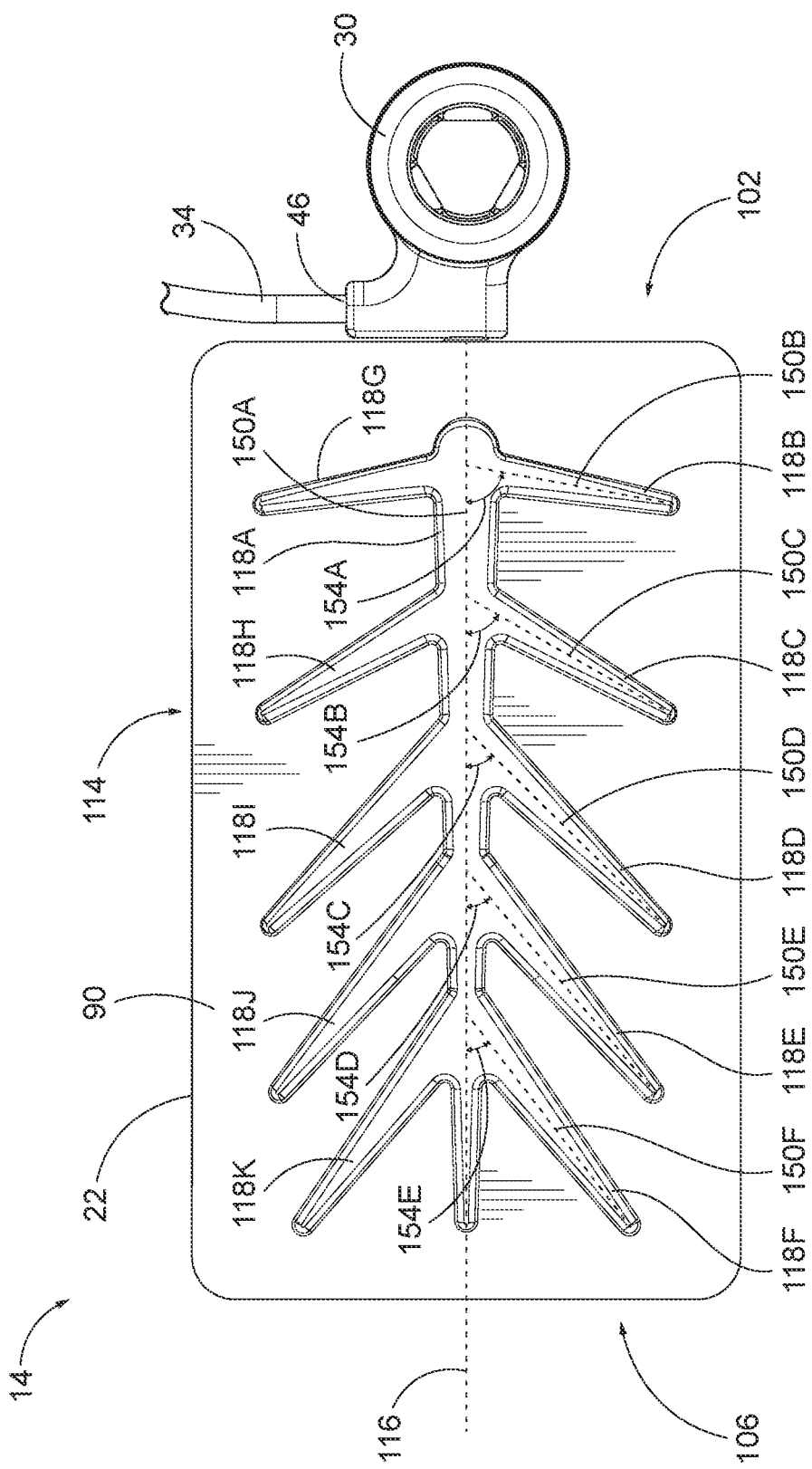
FIG. 6 is a partial side view of the pouch assembly of FIG. 1.

With reference to FIG. 6, the first channel 118A is oriented along a first axis 150A and the second channel 118B is oriented along a second axis 150B. In the illustrated embodiment, the first axis 150A is aligned with the longitudinal axis 116. The second axis 150B intersects the first axis 150A at a first angle 154A. The third channel 118C is oriented along a third axis 150C and the third axis 150C intersects the first axis 150A at a second angle 154B. In the illustrated embodiment, the second angle 154B is smaller than the first angle 154A. In the illustrated embodiment the first angle 154A is approximately 80 degrees, and the second angle 154B is approximately 65 degrees.

With continued reference to FIG. 6, the fourth channel 118D is oriented along a fourth axis 150D and the fourth axis 150D intersects the first axis 150A at a third angle 154C. The fifth channel 118E is oriented along a fifth axis 150E and the fifth axis 150E intersects the first axis 150A at a fourth angle 154D. The sixth channel 118F is oriented along a sixth axis 150F and the sixth axis 150F intersects the first axis 150A at a fifth angle 154E. In the illustrated embodiment, the third angle 154C is smaller than the second angle 154B and the first angle 154A. In some embodiment, the angles 154A-154E reduce in size along the first axis 150A. In other words, the angles positioned closer to the first end 102 (e.g., angles 154A, 154B) are larger than the angles positioned closer to the second end 106 (e.g., angles 154D, 154E).

In the illustrated embodiment, the second plurality of channels 122 in the second wall panel 94 extend away from the first wall panel 90—expanding the volume of the cavity 26. In some embodiments, the second wall panel 94 is identical to the first wall panel 90, which advantageously reduces manufacturing costs.

In some embodiments, the pouch assembly 14 includes a burstable sac 158 (FIG. 4) positioned within the cavity 26. In some embodiments, the burstable sac 158 includes a dose of therapeutic materiel (e.g., vitamins, minerals, fibers, healthy probiotics, water, etc.) administered subsequent to the delivery of the initial feed bolus. When the contents of the burstable sac 158 are due for administration, the sac may be broken through physical manipulation by the user and/or a third party working for the benefit of the user. Alternately, in the absence of physical manipulation the burstable sac may be automatically broken at a pre-determined pressure that is applied by the pump 30. In some embodiment, the breaking of a burstable sac containing clean water may provide a therapeutically-necessary system flush subsequent to bolus delivery. In some embodiments, the burstable sac 158 includes a powered formula, for example, and the fluid in the cavity is water, for example, and the burstable sac 158 is broken open (e.g., ruptured) and mixed with the water prior to the initiation of an infusion. Advantageously, storing the powered formula separated would increase the shelf-life of nutritional formulas.

With reference to FIG. 5, the pump 30 includes a housing 162 with a first clamshell 166A and a second clamshell 166B. In the illustrated embodiment, the housing 162 defines an outer circumferential surface 170. The housing 162 of the pump 30 at least partially receives the stem 134 of the nutrition container 22. In some embodiments, the housing 162 is integrally formed with the nutrition container 22. In the illustrated embodiment, the housing 162 includes a groove 174 formed in the outer circumferential surface 170. In the illustrated embodiment, the groove 174 is formed in the first clamshell 166A. As detailed herein, the groove 174 is configured to receive a detent 178 (e.g., a deformable clip) positioned on the module 18 when the pouch assembly 14 is coupled to the module 18. In some embodiments, the positioning of the groove and detent is reversed with the groove formed on the module and the detent is formed on the housing.

With continued reference to FIG. 5, the pump 30 includes a partial planetary gear set 182 (e.g., partial because the sun gear (e.g., the output member 70) is positioned on the module 18). The housing 162 includes a first ring gear portion 186 and a second ring gear portion 190. In the illustrated embodiment, the first clamshell 166A includes the first ring gear portion 186 and the second clamshell 166B includes the second ring gear portion 190. The housing 162 further includes a channel 194 positioned between the first ring gear portion 186 and the second ring gear portion 190. In the illustrated embodiment, the ring gear portions 186, 190 have a plurality of gear teeth formed therein, and the channel 194 forms a smooth surface.

The pump 30 further includes a carrier 198 positioned within the housing 162. The carrier 198 includes a first end wall 202, a second end wall 206, and a plurality of arms 210 extending between the first end wall 202 and the second end wall 206.

The pump 30 further includes a plurality of planet gears 214 at least partially received within the carrier 198. A portion of each of the plurality of planet gears 214 extends from the carrier 198. In other words, a portion of each planet gear 214 extends between arms 210 beyond an outer boundary of the carrier 198. In the illustrated embodiment, each of the plurality of planet gears 214 is enmeshed with the first ring gear portion 186 and the second ring gear portion 190. In other words, each of the planet gears 214 includes gear teeth 218 enmeshed with both the first ring gear portion 186 and the second ring gear portion 190.

Figure 8:
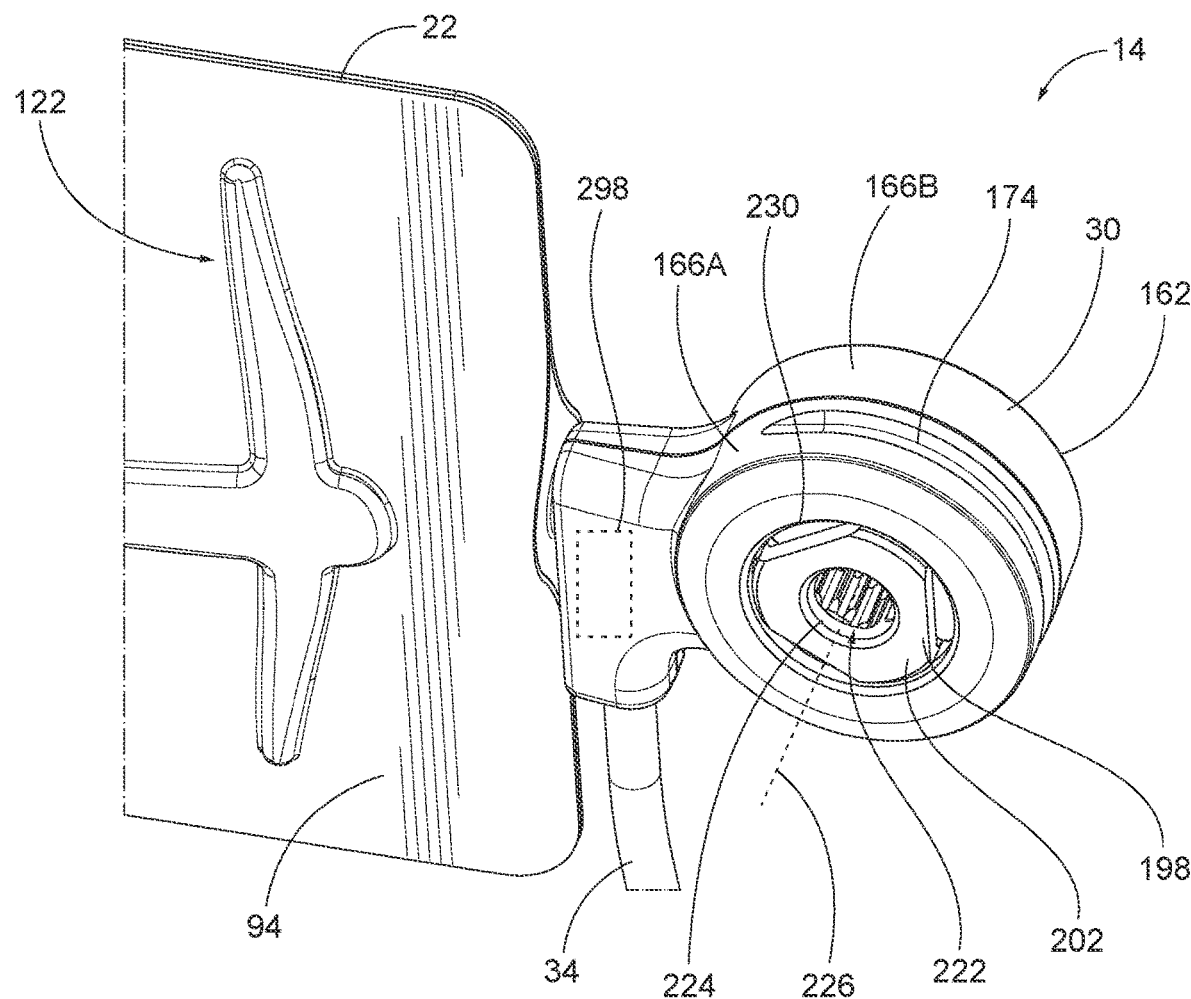
FIG. 8 is a partial rear view of the pouch assembly of FIG. 1.

With reference to FIG. 8, the carrier 198 defines a receptacle 222 positioned between the plurality of planet gears 214. In the illustrated embodiment, the receptacle 222 includes an aperture 224 formed in the first end wall 202 of the carrier 198. As detailed herein, the receptacle 222 is configured to receive the output member 70 of the module 18. In other words, a portion of the module 18 is received within the pump 30 when the pouch assembly 14 is mounted to the module 18.

Figure 7:
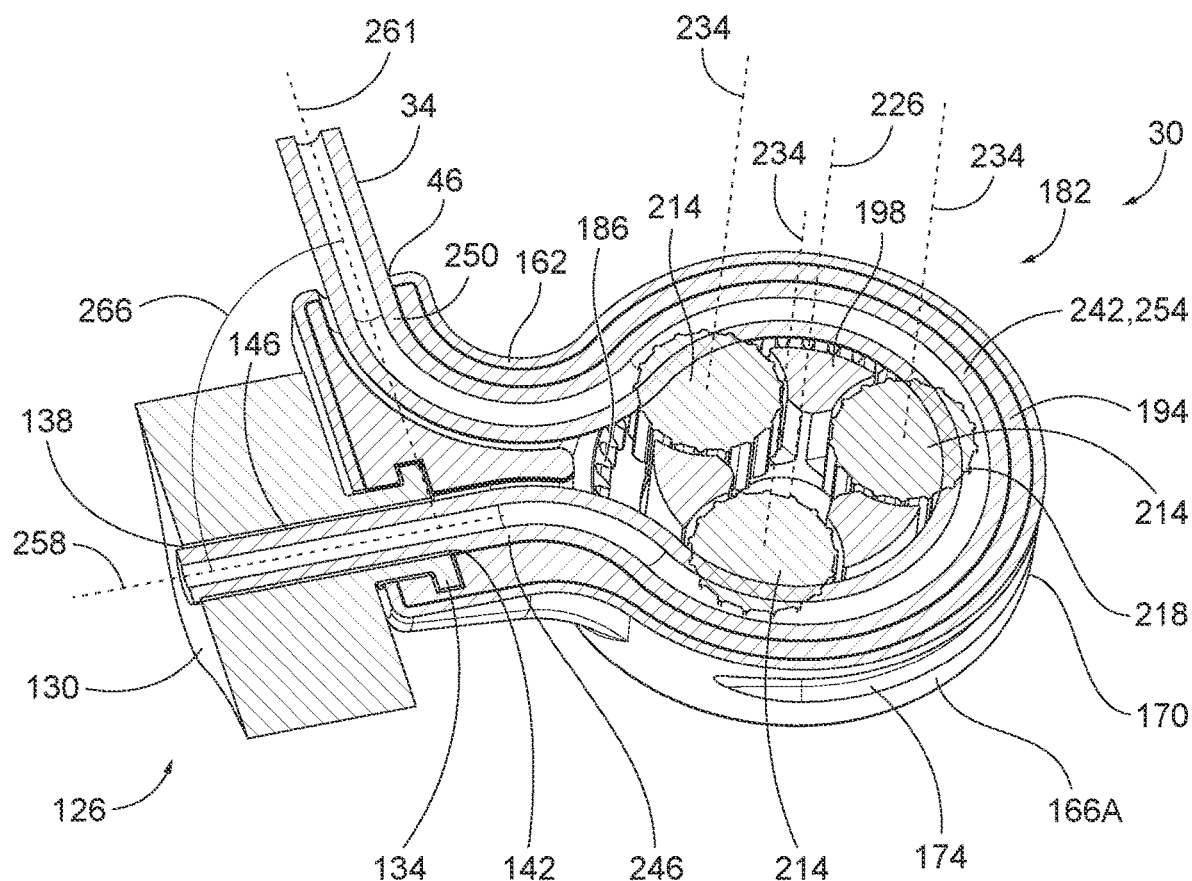
FIG. 7 is a cross-sectional view of a pump of the pouch assembly of FIG. 1.

With reference to FIG. 7, the receptacle 222 defines a center axis 226. The housing 162 of the pump 30 includes an aperture 230 aligned with the receptacle 222. In other words, the aperture 230 on the housing 162 exposes the receptacle 222, making the receptacle 222 accessible. Each of the plurality of planet gears 214 define a planet axis 234, and each planet axis 234 is spaced from and parallel to the center axis 226. In the illustrated embodiment, the output member 70 is aligned with the center axis 226 when the pouch assembly 14 is mounted to the module 18. In some embodiments, the center axis 226 is orthogonal to the longitudinal axis 116 of the nutrition container 22.

With reference to FIG. 5, the pump 30 includes an idler gear 238 positioned within the carrier 198. In the illustrated embodiment, the idler gear 238 is aligned with the center axis 226. The idler gear 238 is enmeshed with the plurality of planet gears 214 and maintains the relative spacing between the planet gears 214.

With continued reference to FIG. 5 and FIG. 7, the pump 30 includes a tube 242 with an inlet portion 246, an outlet portion 250, and an intermediate portion 254 positioned between the inlet portion 246 and the outlet portion 250. In some embodiments, the tube 242 positioned within the pump 30 is the same tube as the tube 34 extending from the pump 30. The inlet portion 246 extends at an inlet axis 258 and the outlet portion 250 extends at an outlet axis 262 (FIG. 7). The inlet axis 258 and the outlet axis 262 intersect at an angle 266. In the illustrated embodiment, the angle 266 is approximately 90 degrees. In some embodiments, the angle 266 is within a range of approximately 45 degrees to approximately 135 degrees. Advantageously, the angle 266 is such that the outlet portion 250 is directed toward the user's gastric access point when the wearable fluid delivery system 10 is worn by a user, which minimizes the total length of tubing needed.

In some embodiments, the pump does not include a carrier (e.g., the pump 30 without the carrier 198. For example, the spacing of the planet gears 214 is maintained by the idler gear 238 without the need for a carrier. Without a carrier, the pump can maintain performance while reducing noise, friction, and inefficiencies associated with a carrier. In a pump embodiment with no carrier, a receptacle (e.g., the receptacle 222) remains positioned between the plurality of planet gears 214.

With continued reference to FIG. 5 and FIG. 7, the tube 242 of the pump 30 is positioned at least partially within the channel 194 formed in the housing 162. In other words, the tube 242 is positioned between the first ring gear portion 186 and the second ring gear portion 190. At least one of the planet gears 214 is in contact with the intermediate portion 254 of the tube 242. In some embodiments, each of the plurality of planet gears 214 is in contact with the intermediate portion 254 of the tube 242. In some embodiments, the gear teeth 218 on the plurality of planet gears 214 is in direct contact with the tube 242. As detailed herein, direct contact of the planet gears 214 with the tube 242 cause the tube 242 to deflect and to pump fluid through the tube 242 from the inlet portion 246 to the output portion 250 (e.g., in a peristaltic manner). Advantageously, direct contact of the gear teeth 218 with the tube results in increased compression force of the tube and increased efficiency gains.

In some embodiments the pump 30 has a flow rate within a range of approximately 1.00 ml/hour and approximately 1800 ml/hour. In some embodiments, the pump 30 is configured to pump a fluid with a dynamic viscosity within a range of approximately 1.0 centipoise (cP) and approximately 500 centipoise (cP). In some embodiments, the pump 30 is configured to deliver a small dose of fluid through the tube 34 at a time that is no more than approximately 1 ml.

Figure 11:
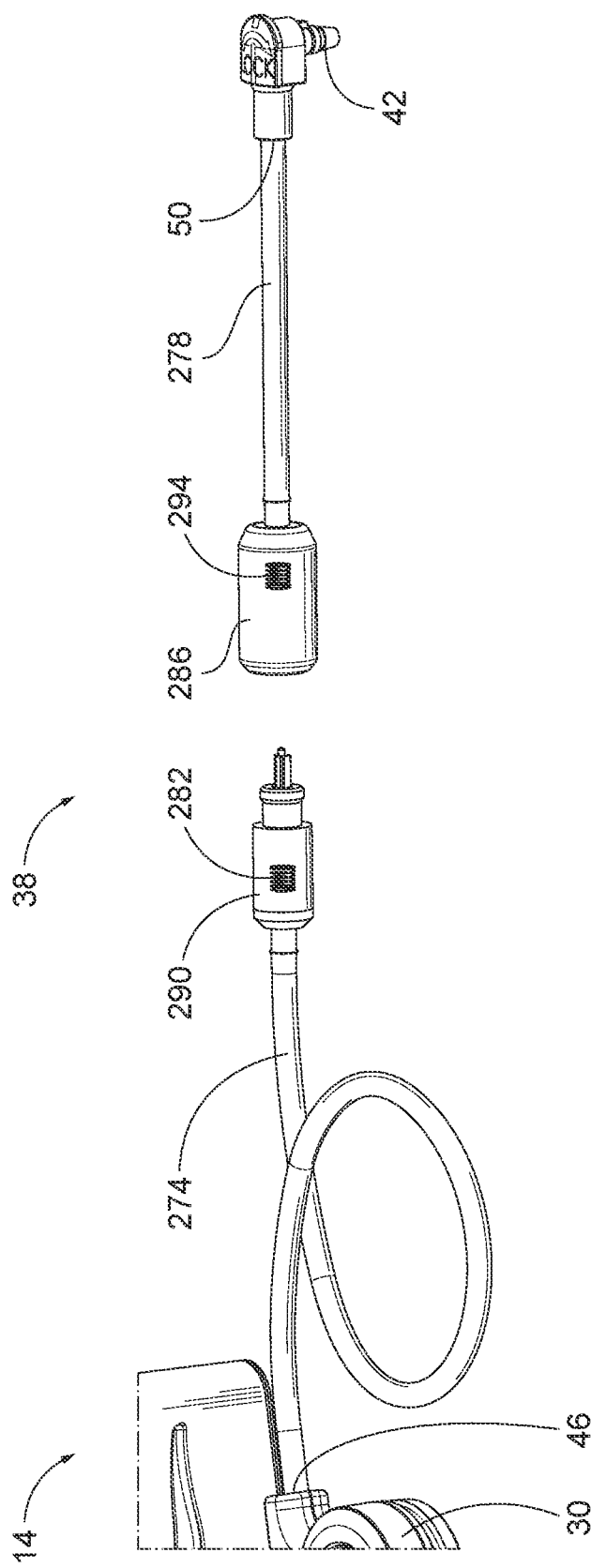
FIG. 11 is a perspective view of a tube assembly including an inline disconnect of the pouch assembly of FIG. 1.

With reference to FIG. 11, the tube 34 extends from the pump 30 to the end connector 42, which is configured to attach to a patient at, for example, a gastric access port. In other words, the end connector 42 is coupled to the outlet 50 (e.g., distal end) of the tube 34, and the end connector 42 is configured to couple to a patient (e.g., at a gastric access port). Such a gastronomy access device is described in U.S. patent application Ser. No. 17/843,397, filed Jun. 27, 2022, the entire contents of which are incorporated herein by reference. In some embodiments, the tube 34 has a length extending from the pump 30 within a range of approximately 10 cm to approximately 30 cm. In some embodiments, the tube 34 has a length extending from the pump 30 of no more than approximately 20 cm. Advantageously, the length of the tube 34 extending from the pump 30 is minimized to avoid unwanted entanglements with the tube 34.

With continued reference to FIG. 11, the breakaway coupling 38 (e.g., a quick-disconnect) of the pouch assembly 14 is coupled to the tube 34 between the pump 30 and the end connector 42 (e.g., between the inlet 46 and the outlet 50). The breakaway coupling 38 is configured to separate in response to a threshold force and seal an upstream portion 274 and a downstream portion 278 of the tube 34 upon separating. The breakaway coupling 38 is coupled in line with the tube 34 (e.g., positioned between the upstream portion 274 and the downstream portion 278). The breakaway coupling 38 includes a first body 282 coupled to the upstream portion 274 and a second body 286 coupled to the downstream portion 278. The first body 282 includes a first biased member 290 that seals the upstream portion 274 when the first body 282 is separated from the second body 286. The second body 286 includes a second biased member 294 that seals the downstream portion 278 when the second body 286 is separated from the first body 282. When the first body 282 and the second body 286 are coupled together, the biased members 290, 294 are forced open, permitting a flow of fluid through the tube 34. Advantageously, the downstream tube portion 278 attached to a user will separate from the upstream portion 274 and the remaining pouch assembly 14 if a threshold force is applied, reducing the risk of ripping the gastric access port out of the patient. Also, the breakaway coupling 38 advantageously seals both tube portions 274, 278 to seal both the cavity 26 and the stomach contents of a patient when the bodies 282, 286 are separated.

In some embodiments, a sensor is configured to detect the pressure within the tube 34. In some embodiments, the sensor is at least partially positioned within the tube 34. Sensors positioned within the tube typically present challenges related to sterilization, but the pouch assembly 14 is a single use disposable and therefore enables the use of more invasive sensors positioned in the tubing without concern for post-use sterilization.

In operation, the pouch assembly 14 is a single-use device that is releasably coupled to the module 18 without the use of tools. In particular, the drive output member 70 on the module 18 is received within the pump 30 as the pump housing 162 is positioned within the recess 78 formed on the module 18. In some embodiments, the output member 70 interfaces with the planet gears 214 in a self-aligning manner. In other words, the pinion does not have to be positioned in a particular orientation to accept the pump attachment. When pressing the pump 30 onto the module 18, the gears 70, 214 will adjust to allow a seamless push down. With the pump housing 162 positioned in the recess 78, the detent 178 is received within the groove 174. In other words, the detent 178 is configured to be received within the groove 174 on the pump 30 when the pouch assembly 14 is coupled to the module 18. When the feeding is complete or the nutrition container 22 empty, the pouch assembly 14 is removed from the module 18 without the use of tools and discarded.

In some embodiments, the pouch assembly 14 self-primes in response to being attached to the module 18. In other words, when the module 18 detects the pouch assembly 14 has been attached, the electric motor 66 is energized to drive the pump 30 for a predetermined time period, which pumps fluid from the cavity 26 to the end connector 42. Advantageously, the self-priming of the system 10 offers user convenience and removes possible user error.

In some embodiments, the pouch assembly 14 includes a machine-readable identifier 298. In some embodiments, the machine-readable identifier 298 is a radio frequency identification (RFID) tag, a quick response (QR) code, a barcode, a near field communication (NFC) coupling, or other suitable communication device. The module 18 includes a sensor 302 (e.g., a wireless reader) that detects the machine-readable identifier 298. In some embodiments, the sensor 302 is the same as the sensor 82. In some embodiments, the machine-readable identifier 298 is representative of a characteristic of the fluid contained within the cavity 26. In some embodiments, the characteristic is a volume, a caloric count, formula type, or a nutritional value. In some embodiments, the characteristic is an expiration date, possible allergens, or possible drug interaction corresponding to a user profile.

In some embodiments, the machine-readable identifier 298 is representative of whether the pump 30 has been attached to the module 14 previously (e.g., to ensure the pump 30 remains single use). In some embodiments, the machine-readable identifier 298 is representative of whether the pump 30 is compatible with the module 14. In some embodiments, the machine-readable identifier 298 is representative of a manufacturing lot number and may relate to a possible recall. In some embodiments, the machine-readable identifier 298 is a QR code positioned on the pump 30, with a corresponding clear housing portion of the module 18. The sensor 302 is a QR reader that detects the QR code through the clear housing portion when the pouch assembly 14 is mounted onto the module 18. In short, the machine-readable identifier 298 on the pouch assembly 14 is detected by the sensor 302 in the module 14 to relay information about the pouch assembly 14 to the processor 58.

Figure 12:
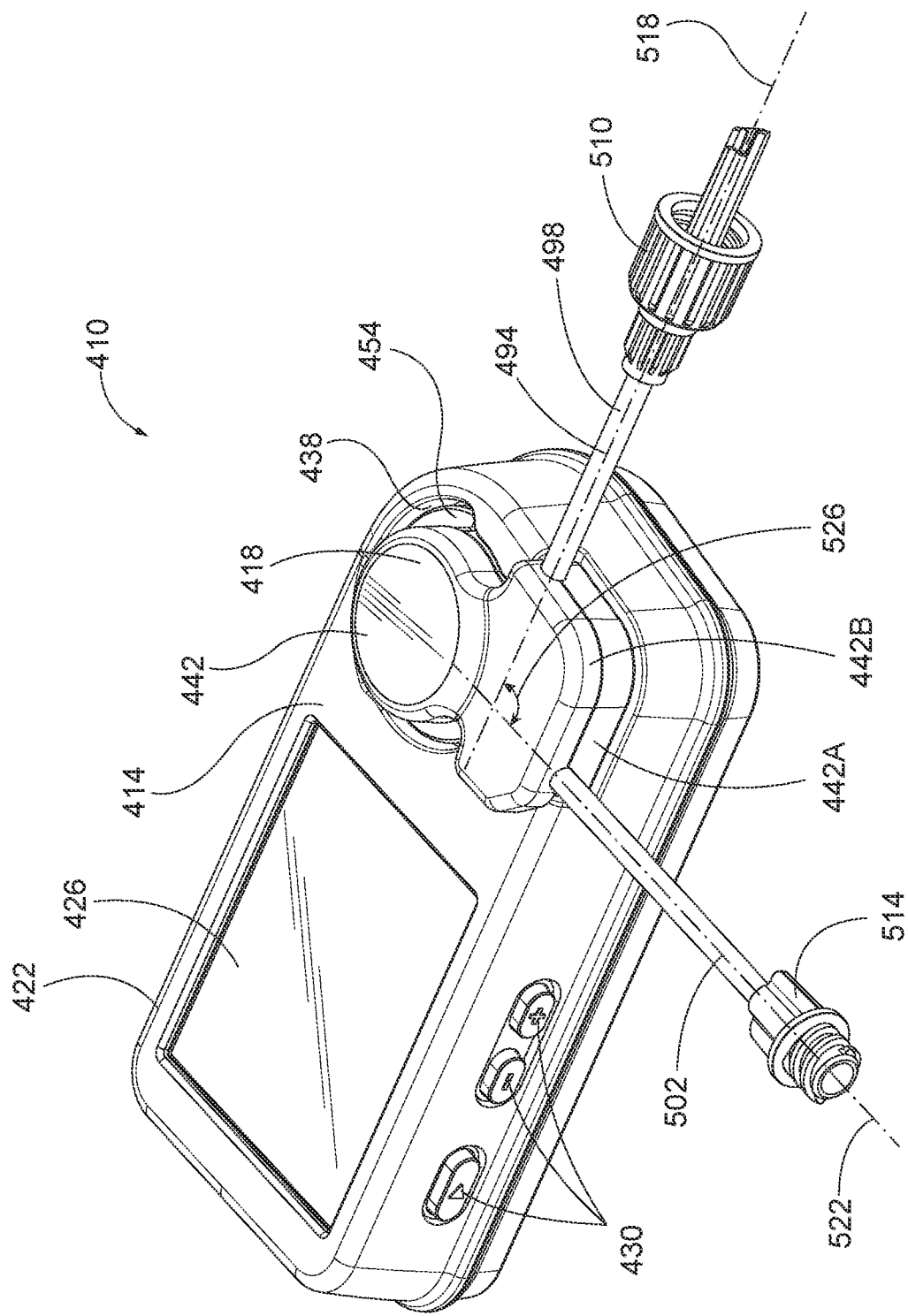
FIG. 12 is a perspective view of a wearable fluid delivery system including a module and a pump assembly.
Figure 13:
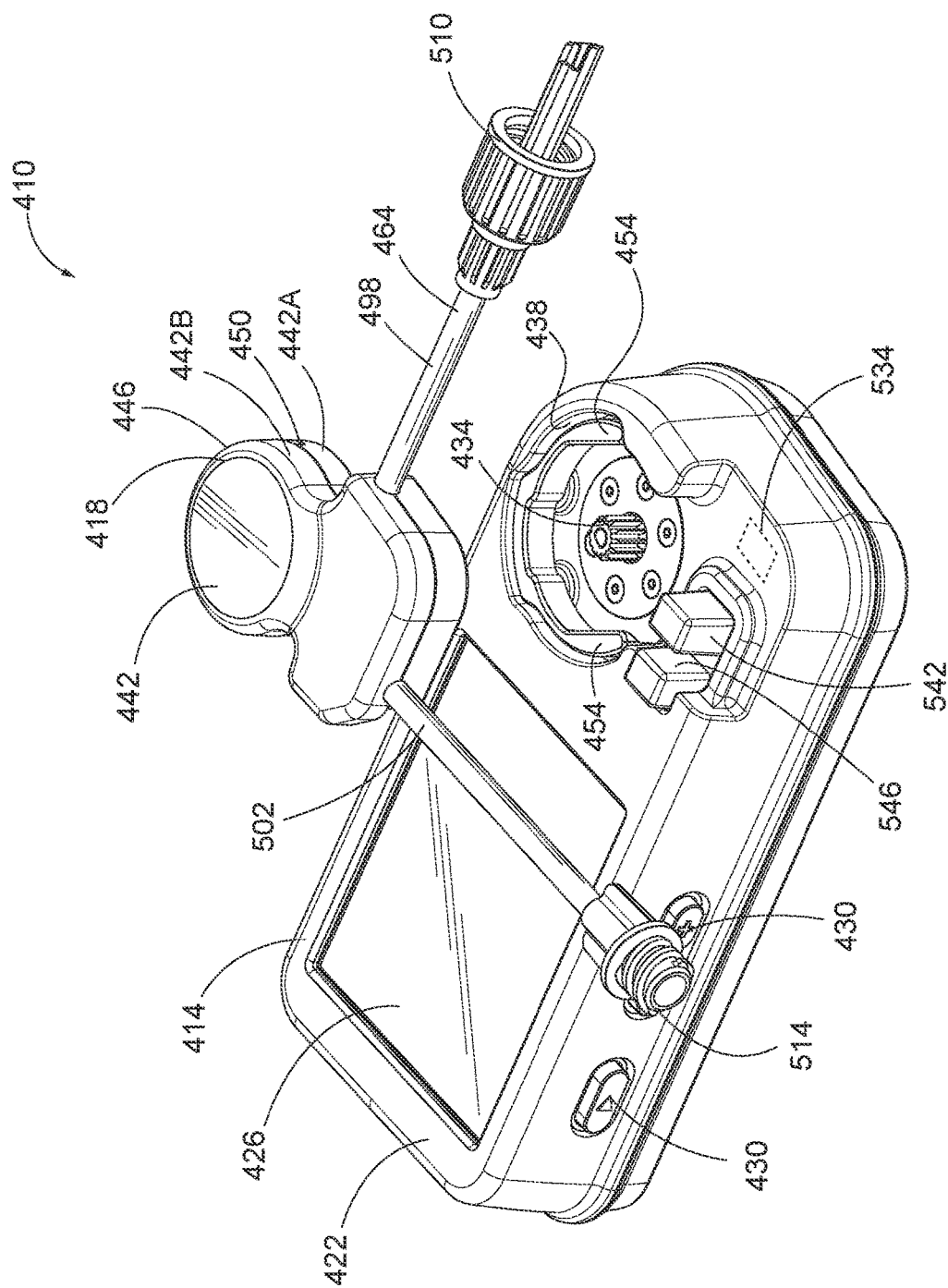
FIG. 13 is a perspective view of the pump assembly removed from the module of FIG. 12.

With reference to FIGS. 12 and 13, a wearable fluid delivery system 140 is shown with a module 414 and a pump assembly 418 removably coupled to the module 414. In some embodiments, the system 410 further includes a nutrition container (e.g., similar to the nutrition container 22) removably coupled to the pump assembly 418 with the nutrition container in fluid communication with the pump assembly 418.

In the illustrated embodiment, the module 414 includes a housing 422, a display screen 426, and buttons 430. Similar to the module 18, the module 414 further includes a processor, a battery, and an electric motor with an output member 434 (e.g., an output gear). The processor is configured to operate the electric motor. In the illustrated embodiment, the module 414 includes a recess 438 and the pump assembly 418 is at least partially received within the recess 438. As detailed herein, the output member 434 is received within the pump assembly 418 when the pump assembly 418 is positioned within the recess 438.

Figure 14:
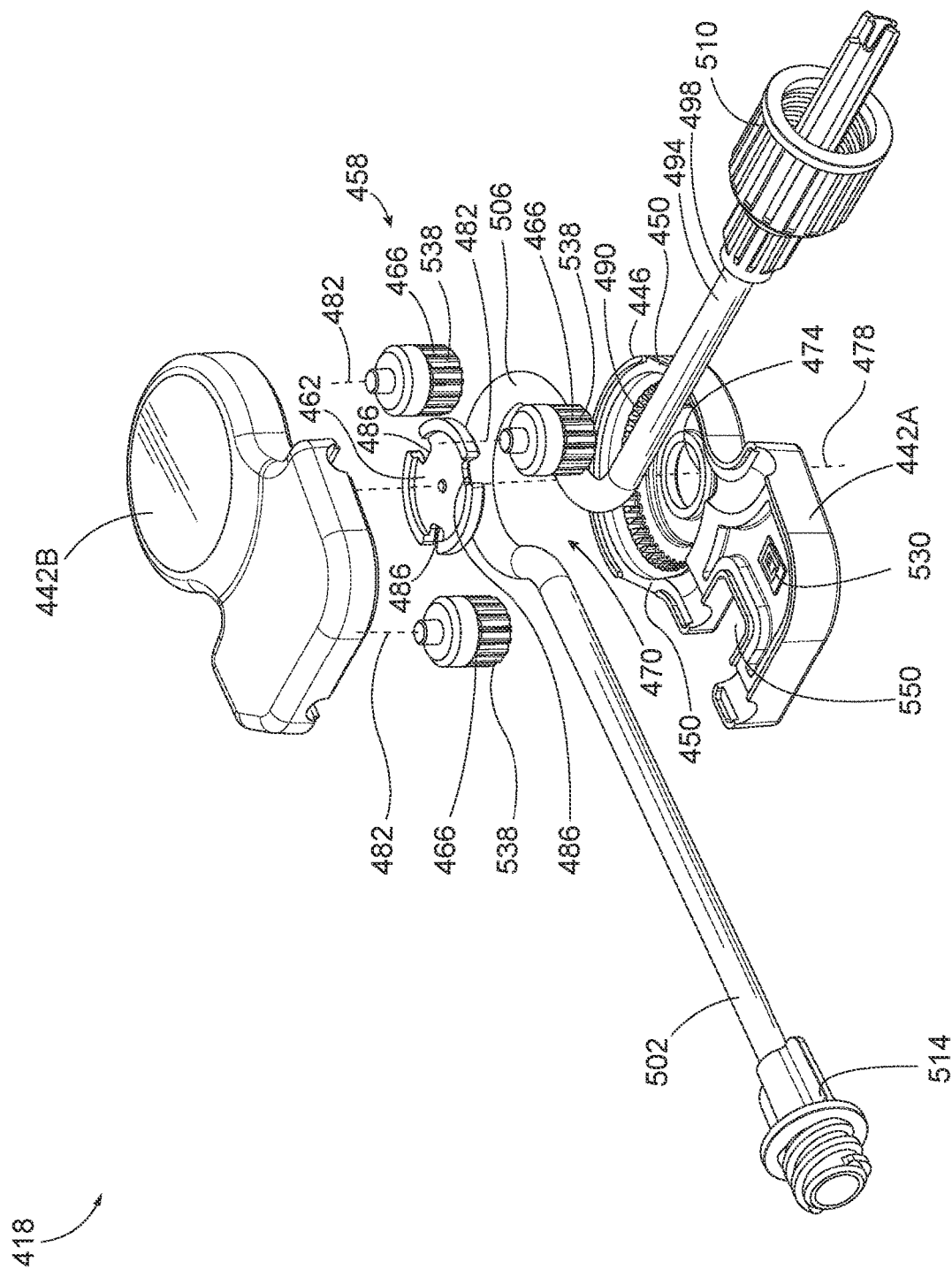
FIG. 14 is an exploded view of the pump assembly of FIG. 12.
Figure 15:
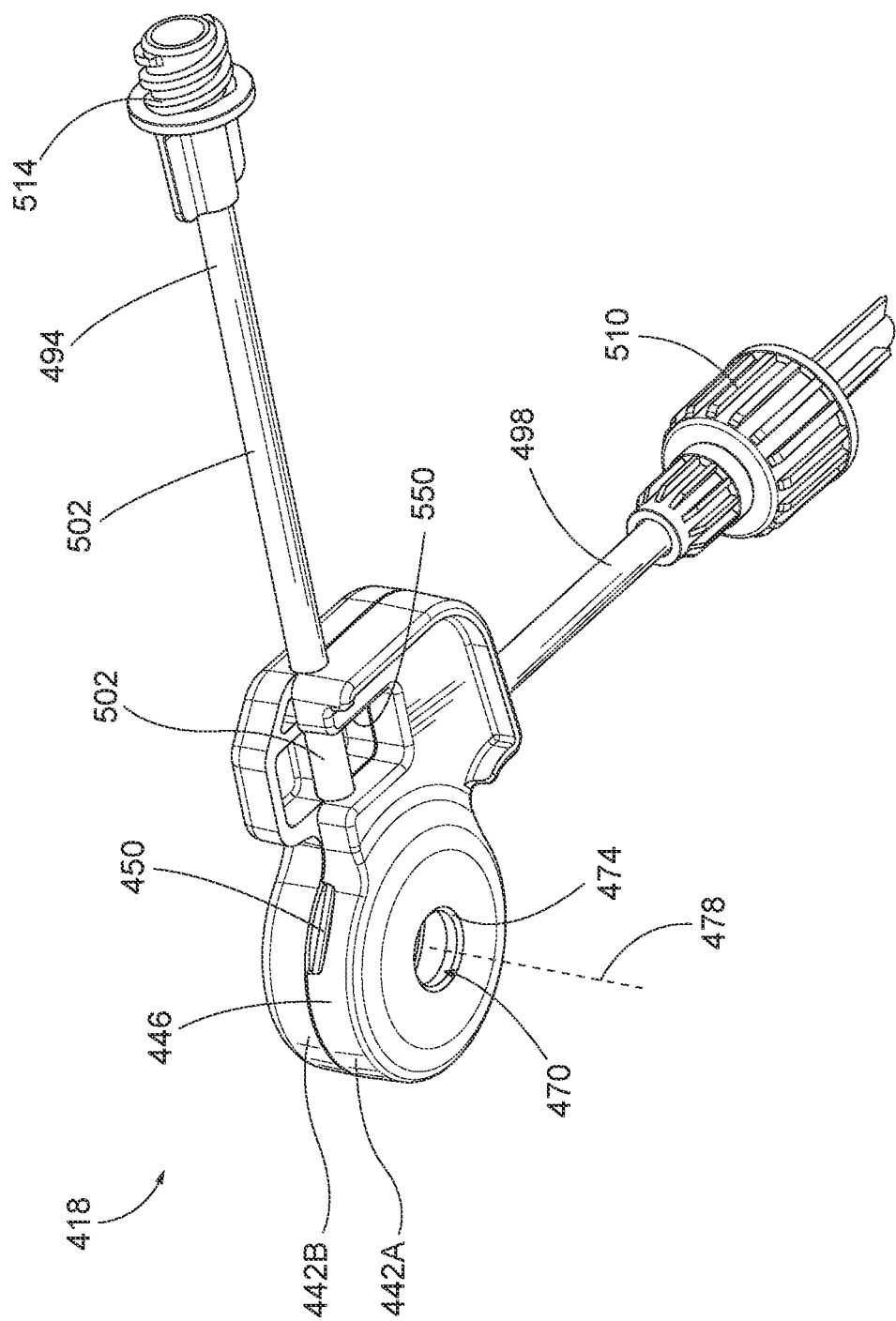
FIG. 15 is a bottom perspective view of the pump assembly of FIG. 12.
Figure 16:
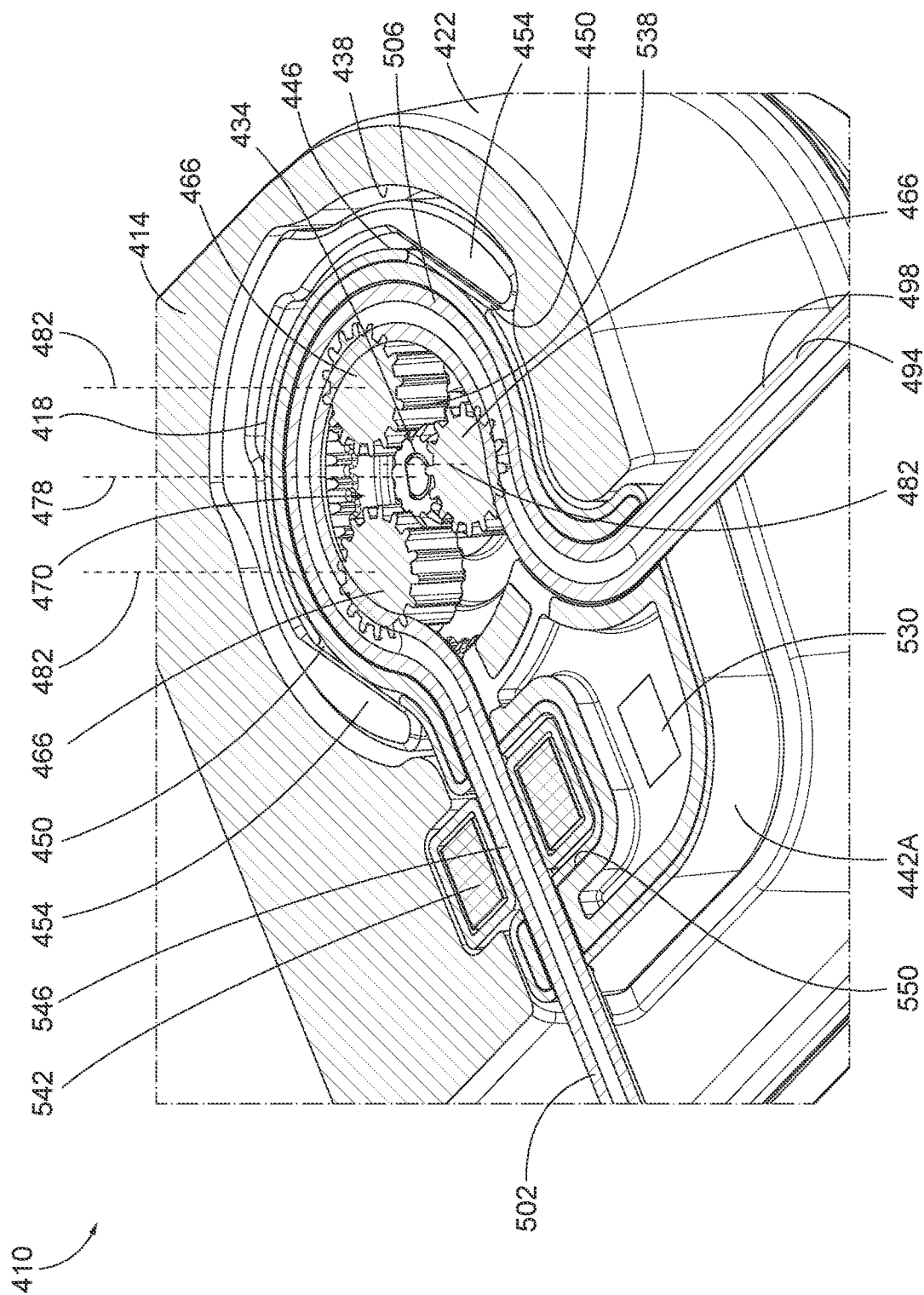
FIG. 16 is a partial perspective view of a cross-section through the module and the pump assembly of FIG. 12.

With reference to FIGS. 14 and 15, the pump assembly 418 includes a housing 442 with a first clamshell 442A and a second clamshell 442B. In the illustrated embodiment, the housing 442 defines an outer circumferential surface 446. In the illustrated embodiment, the housing 442 includes two grooves 450 formed in the outer circumferential surface 446. In the illustrated embodiment, the grooves 450 are formed entirely in the first clamshell 442A. With reference to FIG. 16, the grooves 450 are configured to receive a detent 454 (e.g., a deformable C-clip) positioned on the module 414 when the pump assembly 418 is coupled to the module 414. The pump assembly 418 is a single-use device. In some embodiments, a nutrition container with fluid is releasably coupled to the pump assembly 418. In some embodiments, more than one nutrition container may be coupled to the pump assembly 418 within a "single-use" of the pump assembly 418.

With continued reference to FIG. 14, the pump assembly 418 includes a partial planetary gear set 458 (e.g., partial because the sun gear (e.g., the output member 434) is positioned on the module 414). The partial planetary gear set 458 includes a carrier 462 positioned within the housing 422 and a plurality of planet gears 466 coupled to the carrier 462. A receptacle 470 is positioned between the plurality of planet gears 466. In other words, the receptacle 470 is at least partially formed by space between planet gears 466. The receptacle 470 is configured to receive the output member 434 mounted on the module 414. In the illustrated embodiment, the housing 422 includes an aperture 474 that defines a center axis 478 and is aligned with the receptacle 470. When the pump assembly 418 is mounted on the module 414, the output member 434 is aligned with the center axis 478.

With continued reference to FIG. 14, in the illustrated embodiment, each of the plurality of planet gears 466 defines a planet axis 482 that is spaced from and parallel to the center axis 478. In the illustrated embodiment, the planet gears 466 are at least partially received within notches 486 formed in the carrier 462. A portion of each of the plurality of planet gears 466 extends radially outward from the carrier 462. In other words, a portion of each planet gear 466 beyond an outer boundary of the carrier 462. In the illustrated embodiment, the housing 422 includes a ring gear portion 490 and each of the plurality of planet gears 466 is enmeshed with the ring gear portion 490. In some embodiments, the housing 442 does not include a ring gear portion.

With continued reference to FIG. 14, the pump assembly 418 includes a tube 494 with an inlet portion 498, an outlet portion 502, and an intermediate portion 506 positioned between the inlet portion 498 and the outlet portion 502. In the illustrated embodiment, the inlet portion 498 includes a first removable connector 510 and the outlet portion 502 includes a second removable connector 514. In other words, the pump assembly 418 is removably coupled to a nutrition container and to a patient access port. The inlet portion 498 extends at an inlet axis 518 and the outlet portion 502 extends at an outlet axis 522 (FIG. 12). The inlet axis 518 and the outlet axis 522 intersect at an angle 526. In the illustrated embodiment, the angle 526 is approximately 90 degrees. In some embodiments, the angle 526 is within a range of approximately 45 degrees to approximately 135 degrees. Advantageously, the angle 526 is such that the outlet portion 502 is directed toward the user's gastric access point when the wearable fluid delivery system 410 is worn by a user, which minimizes the total length of tubing needed. In some embodiments, the outlet portion 502 of the tube 494 has a length extending from the housing 442 of no more than approximately 20 cm.

With continued reference to FIGS. 13 and 14, the pump assembly 418 further includes a wireless identification tag 530 (e.g., a machine-readable identifier, a RFID tag) positioned within the housing 442, and the module 414 includes a sensor 534 (e.g., a RFID reader, an antenna) configured to detect the wireless identification tag 530. In some embodiments, sensor 534 is configured to detect when the pump assembly 418 is coupled to the module 414 by detecting the wireless identification tag 530. In some embodiments, the processor does not energize the electric motor unless the sensor 534 detects the pump assembly 418 is fully and properly coupled to the module 414.

With reference to FIG. 16, the intermediate portion 506 of the tube 494 is positioned within the housing 442 and is in contact with the plurality of planet gears 466. In the illustrated embodiment, at least one of the planet gears 466 is in contact with the intermediate portion 506 of the tube 494. In some embodiments, each of the plurality of planet gears 466 is in contact with the intermediate portion 506 of the tube 494. In some embodiments, gear teeth 538 on the plurality of planet gears 466 are in direct contact with the tube 494. The pump assembly 418 is releasably coupled to the module 414 such that the output member 434 is coupled to the pump assembly 418 when the pump assembly 418 is coupled to the module. The output member 434 drives the planet gears 466 to cause a fluid to travel through the tube 494. As detailed herein, direct contact of the planet gears 466 with the tube 494 cause the tube 494 to deflect and to pump fluid through the tube 494 from the inlet portion 498 to the output portion 502 (e.g., in a peristaltic manner). Advantageously, direct contact of the planet gears 466 with the tube 494 results in increased compression force of the tube and increased efficiency gains.

With reference to FIG. 13, the module 414 includes a sensor 542 (e.g., an optical sensor) with a recess 546 formed in the sensor 542. The tube 494 is at least partially positioned within the recess 546 when the pump assembly 418 is coupled to the module 414. In the illustrated embodiment, the output portion 502 of the tube 494 is positioned within the recess 546 of the sensor 542. The housing 442 of the pump assembly 418 includes a cutout 550 configured to at least partially receive the sensor 542. In the illustrated embodiment, the cutout 550 is formed in the first clamshell 442A and the second clamshell 442B covers the cutout 550. As such, the housing 442 at least partially covers the optical sensor 542 when the pump assembly 418 is positioned on the module 414, which advantageously blocks ambient light from reaching the optical sensor 542 and interfering with measurements of fluid in the tube 494.

Figure 17:
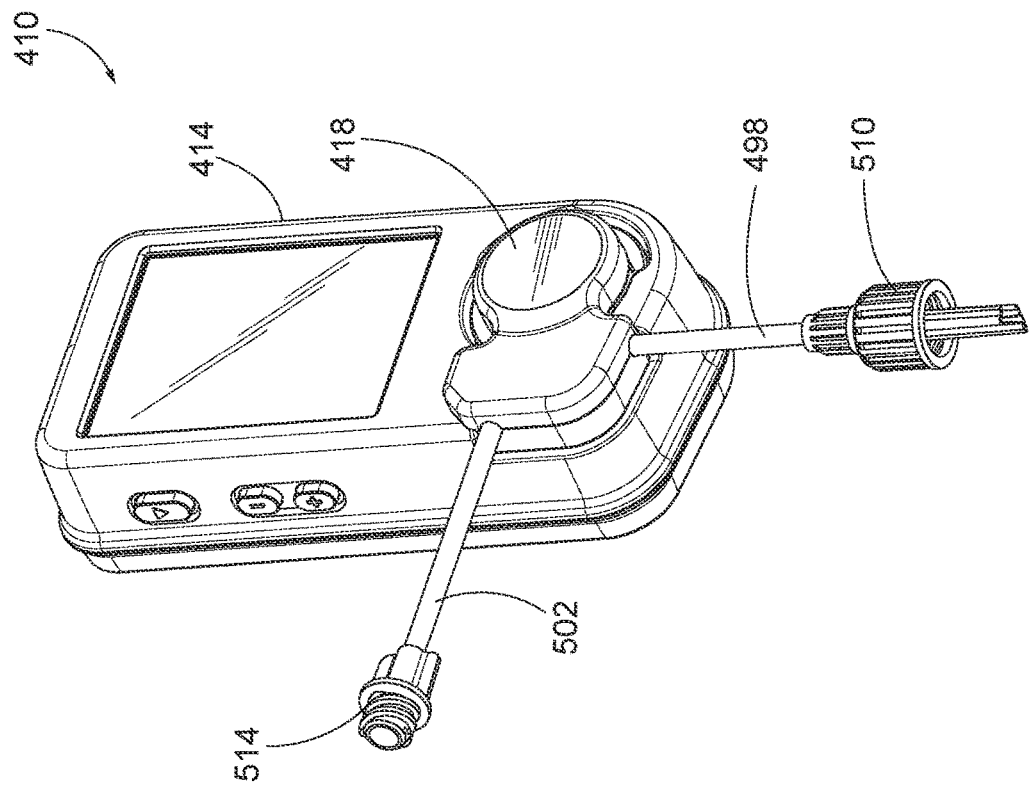
FIG. 17 is an exploded view of a wearable fastener and the module and the pump assembly of FIG. 12.
Figure 17:
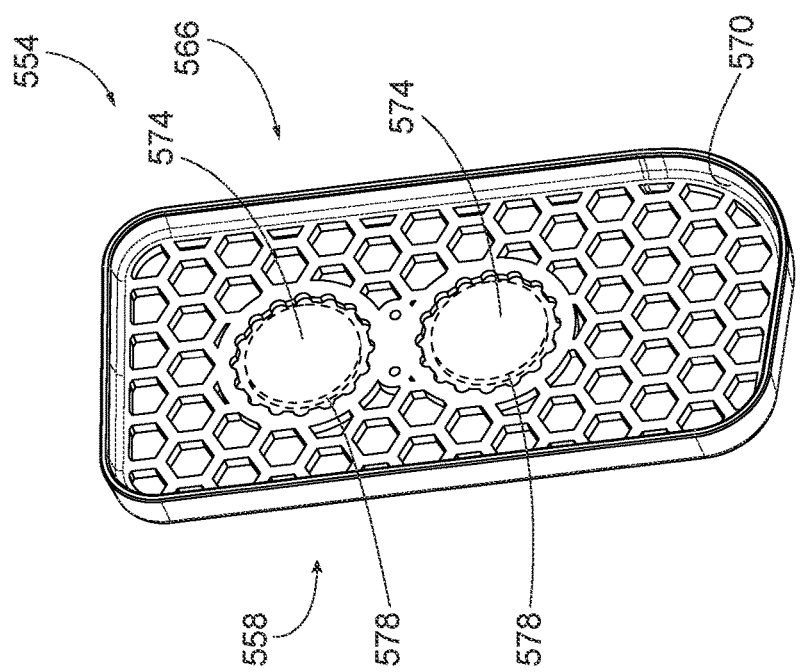
Figure 18:
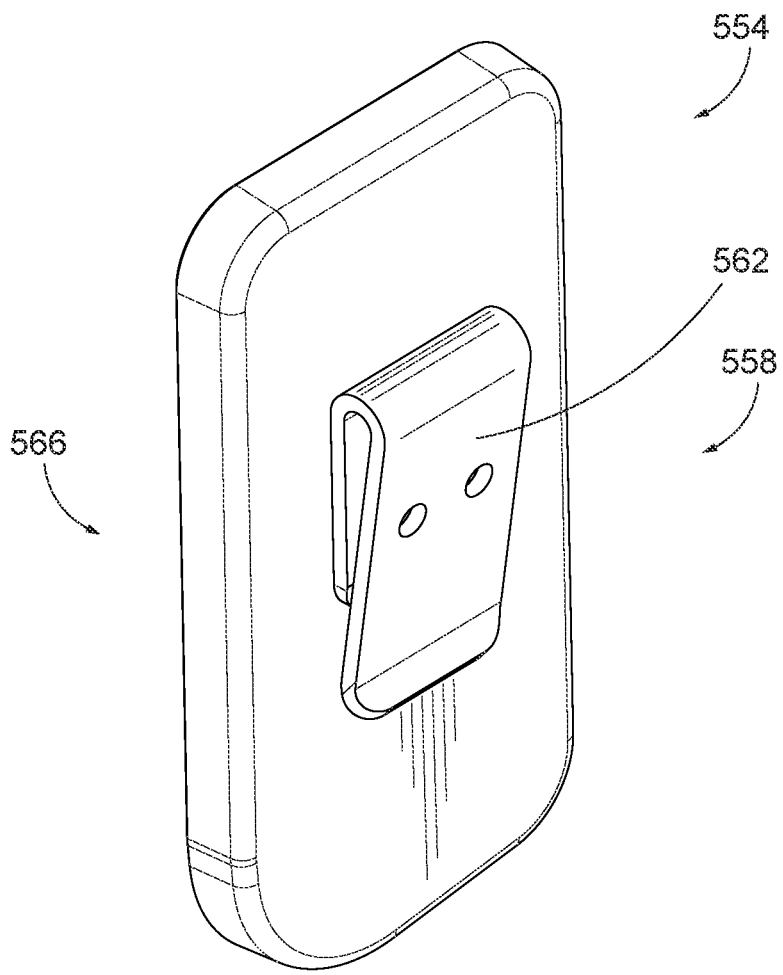
FIG. 18 is a rear view of the wearable fastener of FIG. 17.

With reference to FIG. 17, the system 410 includes a wearable fastener 554 that at least partially receives the module 414. In the illustrated embodiment, the wearable fastener 554 is a mount configured to clip to a user's clothing (e.g., pants) and releasably receive the module 414. With reference to FIGS. 17-18, in the illustrated embodiment, a wearable fastener 554 includes a first side 558 with a clip 562 configured to attach to a user's pants, for example. In the illustrated embodiment, the wearable fastener 554 includes a second side 566, opposite the first side 558, with a recess 570 to at least partially receive the module 414. In some embodiments, the wearable fastener 554 includes at least one magnet 574 to magnetically couple and secure the module 414 to the wearable fastener 554. In other words, the magnet 574 magnetically secures the module 414 to the wearable fastener 554. In the illustrated embodiment, the wearable fastener 554 includes two bores 578 formed in the recess 570, and the bores 578 at least partially receive magnets 574. In some embodiments, the magnets 574 are cylindrical.

Various features and advantages are set forth in the following claims.

What is claimed is:

1. A pump comprising:
   a housing;
   a carrier positioned within the housing;
   a plurality of planet gears coupled to the carrier;
   a receptacle positioned between the plurality of planet gear; and
   a tube with an inlet portion, an outlet portion, and an intermediate portion positioned between the inlet portion and the outlet portion;
   wherein at least one of the plurality of planet gears is in contact with the intermediate portion of the tube; and
   wherein each of the plurality of planet gears includes gear teeth in direct contact with the tube.

2. The pump of claim 1, wherein the receptacle is configured to receive a drive gear mounted on a drive module.

3. The pump of claim 1, wherein the housing includes an aperture aligned with receptacle, wherein the aperture defines a center axis.

4. The pump of claim 3, wherein each of the plurality of planet gears define a planet axis spaced from and parallel to the center axis.

5. The pump of claim 1, wherein the carrier at least partially defines the receptacle positioned between the plurality of planet gears.

6. The pump of claim 5, wherein the receptacle defines a center axis and wherein the housing includes an aperture aligned with the receptacle.

7. The pump of claim 6, wherein each of the plurality of planet gears define a planet axis spaced from and parallel to the center axis.

8. The pump of claim 6, further including a gear positioned within the carrier, wherein the gear is aligned with the center axis.

9. The pump of claim 8, wherein the gear is enmeshed with the plurality of planet gears.

10. The pump of claim 1, wherein a portion of each of the plurality of planet gears extends from the carrier.

11. The pump of claim 1, wherein the housing including a ring gear portion and the plurality of planet gears is enmeshed with the ring gear portion.

12. The pump of claim 11, wherein the ring gear portion is a first ring gear portion and the housing further includes a second ring gear portion and a channel positioned between the first ring gear portion and the second ring gear portion, and wherein the tube is positioned at least partially within the channel.

13. The pump of claim 12, wherein each of the plurality of planet gears is enmeshed with the first ring gear portion and the second ring gear portion.

14. The pump of claim 1, wherein the housing includes an outer surface with a groove formed in the outer surface.

15. The pump of claim 1, wherein the inlet portion extends at an inlet axis, and the outlet portion extends at an outlet axis, and wherein the inlet axis and the outlet axis intersect at an angle.

16. The pump of claim 15, wherein the angle is 90 degrees.

17. The pump of claim 1, further including a wireless identification tag positioned within the housing.

18. The pump of claim 1, wherein the housing includes a cutout configured to at least partially receive a sensor.

19. The pump of claim 1, wherein the inlet portion includes a first removable connector and the outlet portion includes a second removable connector.

20. A pump comprising:
    a housing;
    a carrier positioned within the housing;
    a plurality of planet gears coupled to the carrier;
    a receptacle positioned between the plurality of planet gear; and
    a tube with an inlet portion, an outlet portion, and an intermediate portion positioned between the inlet portion and the outlet portion;
    wherein at least one of the plurality of planet gears is in contact with the intermediate portion of the tube; and
    wherein the inlet portion extends from the housing at an inlet axis, and the outlet portion extends from the housing at an outlet axis, and wherein the inlet axis and the outlet axis intersect at an angle.

21. The pump of claim 20, wherein the angle is 90 degrees.

22. The pump of claim 20, wherein the housing includes an aperture aligned with receptacle, wherein the aperture defines a center axis, and wherein each of the plurality of planet gears define a planet axis spaced from and parallel to the center axis.

23. The pump of claim 22, wherein each of the plurality of planet gears includes gear teeth in direct contact with the tube.

24. The pump of claim 22, wherein the housing including a ring gear portion and the plurality of planet gears is enmeshed with the ring gear portion; and wherein the ring gear portion is a first ring gear portion and the housing further includes a second ring gear portion and a channel positioned between the first ring gear portion and the second ring gear portion, and wherein the tube is positioned at least partially within the channel.

25. The pump of claim 20, further including a wireless identification tag positioned within the housing.

26. A pump comprising:
    a housing;
    a carrier positioned within the housing; a plurality of planet gears coupled to the carrier;
    a receptacle positioned between the plurality of planet gear; and a gear positioned within the carrier;
    wherein the gear is enmeshed with the plurality of planet gears;
    a tube with an inlet portion, an outlet portion, and an intermediate portion positioned between the inlet portion and the outlet portion;
    wherein at least one of the plurality of planet gears is in contact with the intermediate portion of the tube;
    wherein the carrier at least partially defines the receptacle positioned between the plurality of planet gears; wherein the receptacle defines a center axis and wherein the housing includes an aperture aligned with the receptacle;
    wherein the aperture exposes the receptacle; and the receptacle is configured to receive a drive gear mounted on a drive module; and wherein the gear is aligned with the center axis.

27. The pump of claim 26, wherein the inlet portion extends at an inlet axis, and the outlet portion extends at an outlet axis, and wherein the inlet axis and the outlet axis intersect at an angle.

28. The pump of claim 27, wherein each of the plurality of planet gears includes gear teeth in direct contact with the tube.

29. The pump of claim 26, wherein the carrier includes a first end wall, a second end wall, and a plurality of arms extending between the first end wall and the second end wall.

30. The pump of claim 26, further including a wireless identification tag positioned within the housing.

31. A pump comprising:
a housing;
a carrier positioned within the housing;
a plurality of planet gears coupled to the carrier;
a receptacle positioned between the plurality of planet gear; and
a tube with an inlet portion, an outlet portion, and an intermediate portion positioned between the inlet portion and the outlet portion;

wherein at least one of the plurality of planet gears is in contact with the intermediate portion of the tube;

wherein the housing including a ring gear portion and the plurality of planet gears is enmeshed with the ring gear portion;

wherein the ring gear portion is a first ring gear portion and the housing further includes a second ring gear portion and a channel positioned between the first ring gear portion and the second ring gear portion, and wherein the tube is positioned at least partially within the channel.

32. The pump of claim 31, wherein each of the plurality of planet gears is enmeshed with the first ring gear portion and the second ring gear portion.

33. The pump of claim 31, wherein the inlet portion extends at an inlet axis, and the outlet portion extends at an outlet axis, and wherein the inlet axis and the outlet axis intersect at an angle.

34. The pump of claim 33, wherein each of the plurality of planet gears includes gear teeth in direct contact with the tube.

35. The pump of claim 31, further including a wireless identification tag positioned within the housing.

* * * * *

UNITED STATES PATENT AND TRADEMARK OFFICE
CERTIFICATE OF CORRECTION

| | |
|---|---|
| PATENT NO. | : 12,017,039 B2 |
| APPLICATION NO. | : 18/446039 |
| DATED | : June 25, 2024 |
| INVENTOR(S) | : Joseph Neal Piper et al. |

It is certified that error appears in the above-identified patent and that said Letters Patent is hereby corrected as shown below:

In the Claims

Column 17, Claim 1, Line 22 reads:
gear; and

Whereas it should read:
gears; and

Column 18, Claim 20, Line 19 reads:
gear; and

Whereas it should read:
gears; and

Column 18, Claim 26, Line 54 reads:
gear; and a gear positioned within the carrier;

Whereas it should read:
gears; and a gear positioned within the carrier;

Column 19, Claim 31, Line 22 reads:
gear; and

Whereas it should read:
gears; and

Signed and Sealed this
Thirteenth Day of August, 2024

*Katherine Kelly Vidal*
*Director of the United States Patent and Trademark Office*